(12) United States Patent
Majcher et al.

(10) Patent No.: US 11,179,577 B2
(45) Date of Patent: Nov. 23, 2021

(54) SYSTEMS AND METHODS FOR HOT SPOT REDUCTION DURING DESIGN AND MANUFACTURE OF RADIATION THERAPY BOLUS

(71) Applicant: ADAPTIIV MEDICAL TECHNOLOGIES INC., Halifax (CA)

(72) Inventors: Christopher Majcher, Dartmouth (CA); Borko Basaric, Halifax (CA); James L. Robar, Halifax (CA)

(73) Assignee: ADAPTIV MEDICAL TECHNOLOGIES INC., Halifax (CA)

( * ) Notice: Subject to any disclaimer, the term of this patent is extended or adjusted under 35 U.S.C. 154(b) by 54 days.

(21) Appl. No.: 16/832,577

(22) Filed: Mar. 27, 2020

(65) Prior Publication Data

US 2020/0338363 A1 Oct. 29, 2020

Related U.S. Application Data

(60) Provisional application No. 62/839,279, filed on Apr. 26, 2019.

(51) Int. Cl.
*A61N 5/10* (2006.01)

(52) U.S. Cl.
CPC ......... *A61N 5/1031* (2013.01); *A61N 5/1048* (2013.01); *A61N 5/1077* (2013.01);
(Continued)

(58) Field of Classification Search
None
See application file for complete search history.

(56) References Cited

U.S. PATENT DOCUMENTS 6,301,329 B1 10/2001 Surridge
6,703,632 B1 3/2004 Macklis et al.
(Continued)

FOREIGN PATENT DOCUMENTS

WO 2013115607 A2 8/2013

OTHER PUBLICATIONS

Perkins et al. "A Custom Three-dimensional Electron Bolus Technique for Optimization of Postmastectomy Irradiation". Int. J. Radiation Oncology Biol. Phys. 51.4 (2001): 1142-1151.
(Continued)

*Primary Examiner* — Hoon K Song
(74) *Attorney, Agent, or Firm* — Hill & Schumacher

(57) ABSTRACT

Systems and methods are provided for designing and/or modifying a radiation therapy bolus for the reduction of hot spots. A digital bolus model may be modified based on the identification of a peak in the outer surface of the digital bolus model, where the peak satisfies search criteria associated with the generation of a hot spot through scattering from the peak. The digital bolus model is modified within a region surrounding the peak to smooth the peak and thereby reduce the intensity of the hot spot. The modified digital bolus model may be employed to fabricate a bolus for use in radiation therapy. The search criteria may be evaluated according to a proximity between a location measure associated with the peak and a location measure associated with the hot spot, optionally when the location measures are projected in a reference plane that resides perpendicular to the beam axis.

34 Claims, 19 Drawing Sheets
(7 of 19 Drawing Sheet(s) Filed in Color)

(52) U.S. Cl.
CPC ............ *A61N 2005/1074* (2013.01); *A61N 2005/1096* (2013.01)

(56) References Cited

U.S. PATENT DOCUMENTS

| | | | |
|---|---|---|---|
| 7,815,826 | B2 | 10/2010 | Serdy et al. |
| 9,927,805 | B2 | 3/2018 | Ju |
| 2002/0106054 | A1 | 8/2002 | Caflisch et al. |
| 2008/0211132 | A1 | 9/2008 | Feenstra |
| 2008/0230074 | A1 | 9/2008 | Zheng et al. |
| 2010/0163726 | A1 | 7/2010 | Shimada et al. |
| 2010/0195793 | A1* | 8/2010 | Nelms ............... A61N 5/103 378/65 |
| 2012/0253495 | A1 | 10/2012 | Wright et al. |
| 2013/0085315 | A1 | 4/2013 | Isham et al. |
| 2015/0006098 | A1* | 1/2015 | Ju ............... G05B 19/41875 702/84 |
| 2015/0094838 | A1 | 4/2015 | MacLaverty |
| 2016/0256709 | A1* | 9/2016 | Robar ............... A61N 5/1031 |

OTHER PUBLICATIONS

Kudchadker et al. "Electron Conformal Radiotherapy Using Bolus and Intensity Modulation". Int. J. Radiation Oncology Biol. Phys. 53.4 (2002): 1023-1037.

Low, et al, "Electron Bolus Design For Radiotherapy Treatment Planning: Bows Design Algorithms", Medical Physics, vol. 19, No. 1, Jan./Feb. 1992, pp. 115-124.

Kudchadker et al: "Utilization of custom electron bolus in head and neck radiotherapy", Journal of Applied Clinical Medical Physics, vol. 4, No. 4, Sep. 1, 2003 (Sep. 1, 2003), pp. 321-333.

PCT Search Report dated Feb. 10, App No. PCT/CA2014/051128, filed Nov. 26, 2014, titled "System and Method for Manufacturing Bolus for Radiotherapy Using a Three-Dimensional Printer," to Dalhousie University.

* cited by examiner

| Bolus Peak-Reduction Value [%] | Maximum dose to PTV [%] | Minimum dose to PTV [%] | Mean dose to PTV [%] | Conformity Index $V_{D95}/V_{PTV}$ | Homogeneity Index $(D_{max}-D_{90})/D_{90}$ |
|---|---|---|---|---|---|
| 100 (uncorrected MEB) | 131.3 | 89.0 | 111.5 | 2.32 | 0.46 |
| 80 | 119.6 | 89.2 | 104.9 | 2.05 | 0.33 |
| 60 | 112.0 | 86.5 | 100.7 | 1.87 | 0.24 |
| 40 | 107.8 | 87.2 | 98.6 | 1.83 | 0.20 |
| 20 | 102.4 | 86.3 | 96.4 | 1.79 | 0.14 |
| 0 (maximally corrected MEB) | 100.8 | 87.0 | 96.6 | 2.01 | 0.12 |
| Simple bolus 5mm | 97.8 | 89.5 | 93.7 | 2.72 | 0.09 |

SYSTEMS AND METHODS FOR HOT SPOT REDUCTION DURING DESIGN AND MANUFACTURE OF RADIATION THERAPY BOLUS

CROSS-REFERENCE TO RELATED APPLICATION

This application claims priority to U.S. Provisional Patent Application No. 62/839,279, titled "SYSTEMS AND METHODS FOR HOT SPOT REDUCTION DURING DESIGN AND MANUFACTURE OF RADIATION THERAPY BOLUS" and filed on Apr. 26, 2019, the entire contents of which is incorporated herein by reference.

BACKGROUND

The present disclosure relates to radiation therapy. In particular, the present disclosure relates to the design and manufacture of a patient-customized custom radiation therapy bolus.

Radiation therapy is a cancer treatment modality used on approximately 50% of all the cancer patients. The modality employs ionizing radiation to eliminate cancer cells utilizing sophisticated imaging data-based computer models for planning the adequate dose to be delivered to the patient in form of precise irradiation of the planning target volume (PTV) and at the same time minimizing damaging effects to the organs at risk.

A certain percent of all radiation therapy treatments require a superficial deposition of dose into the patient tissue. Since megavoltage radiation beams do not efficiently deposit dose on or near the skin surface, a tissue-equivalent compensator called a "bolus" may be used to efficiently bring the prescribed dose closer to the surface of the patient. A bolus is frequently used in electron radiation therapy treatments where a single beam of electrons is being used for treating superficial tumors.

SUMMARY

Systems and methods are provided for designing and/or modifying a radiation therapy bolus for the reduction of hot spots. A digital bolus model may be modified based on the identification of a peak in the outer surface of the digital bolus model, where the peak satisfies search criteria associated with the generation of a hot spot through scattering from the peak. The digital bolus model is modified within a region surrounding the peak to smooth the peak and thereby reduce the intensity of the hot spot. The modified digital bolus model may be employed to fabricate a bolus for use in radiation therapy. The search criteria may be evaluated according to a proximity between a location measure associated with the peak and a location measure associated with the hot spot, optionally when the location measures are projected in a reference plane that resides perpendicular to the beam axis.

Accordingly, in one aspect, there is provided a method of fabricating a bolus for use in radiation therapy, the method comprising:
  obtaining a digital bolus model, the digital bolus model defining an outer surface and an inner surface, wherein the inner surface is shaped to conformally contact a subject during radiation therapy;
  identifying a hotspot associated with the digital bolus model;
  processing the digital bolus model to identify, within the outer surface, a local maximum satisfying search criteria, the search criteria associating the local maximum with generation of the hotspot;
  refining the digital bolus model by modifying a subregion of the outer surface to reduce an intensity of the hotspot, the subregion including the local maximum, thereby obtaining a refined digital bolus model; and
  fabricating the bolus according to the refined digital bolus model.

In one implementation of the method, the local maximum is determined to satisfy the search criteria associated with the hotspot by: determining a hotspot location measure associated with a location of the hotspot and a local maximum location measure associated with a location of the local maximum; and determining that the hotspot location measure and the local maximum location measure satisfy proximity criteria.

The step of determining that the hotspot location measure and the local maximum location measure satisfy proximity criteria may comprise: projecting one or both of the hotspot location measure and the local maximum location measure, such that after projection, the hotspot location measure and the local maximum location measure reside within a common two-dimensional region; and determining that the hotspot location measure and the local maximum location measure satisfy the proximity criteria within the common two-dimensional region.

The local maximum may be determined to satisfy the proximity criteria associated with the hotspot by: projecting the hotspot location measure onto the outer surface, thereby obtaining a projected hotspot location measure; and determining that the projected hotspot location measure and the local maximum location measure satisfy the proximity criteria.

The local maximum may be determined to satisfy the proximity criteria associated with the hotspot by: projecting the hotspot location measure and the local maximum location measure onto a reference plane that is perpendicular to a beam axis defined by a treatment plan associated with the subject, thereby obtaining a projected hotspot location measure and a projected local maximum location measure; and determining that the projected hotspot location measure and the projected local maximum location measure satisfy the proximity criteria.

The hotspot location measure may be a location of a center of the hotspot and the local maximum location measure is a location of the local maximum, wherein determining that the projected hotspot location measure and the projected local maximum location measure satisfy proximity criteria comprises determining that a projection of the location of the center of the hotspot onto the reference plane and a projection of the location of the local maximum onto the reference plane have a separation less than a separation threshold. The hotspot location measure may be a three-dimensional hotspot margin surrounding the hotspot, and wherein determining that the projected hotspot location measure and the projected local maximum location measure satisfy proximity criteria comprises determining that a projection of the three-dimensional hotspot margin onto the reference plane spatially overlaps with a projection of the local maximum location measure onto the reference plane.

The three-dimensional hotspot margin may be user-configurable. The method may further comprise displaying, in a user interface, a visual representation of the three-dimensional hotspot margin.

The local maximum location measure may demarcate a peak region surrounding the local maximum, and wherein determining that the projected hotspot location measure and the projected local maximum location measure satisfy proximity criteria comprises determining that the projection of the three-dimensional hotspot margin onto the reference plane spatially overlaps with a projection of the peak region surrounding the local maximum. The peak region may be user-configurable. The peak region may extend to a valley, such that beyond the valley, a height contour associated with the outer surface does not enclose the local maximum. The subregion over which the outer surface is modified may be the peak region.

In another implementation of the method, the reference plane tangentially contacts the subject.

In another implementation of the method, the local maximum may be identified by: obtaining height data characterizing a height of the outer surface relative to a height evaluation plane, wherein the height evaluation plane is perpendicular to the beam axis; and processing the height data to locate the local maximum. The outer surface may be modified with the subregion by smoothing the outer surface within the subregion to reduce a height of the local maximum. The height evaluation plane may tangentially contact the subject.

In another implementation of the method, the hotspot is identified based on a hotspot RT structure exported by a treatment planning system.

In another implementation of the method, the hotspot is identified by processing dose data obtained from a treatment planning system.

In another implementation of the method, the hotspot is identified by processing dose data obtained by performing a pencil beam dose calculation.

In another implementation of the method, the hotspot is identified, at least in part, based on input received from a user.

In another implementation of the method, the method further comprises receiving input from a user, the input confirming the association of the local maximum with the hotspot, prior to refining the digital bolus model.

In another implementation of the method, the method further comprises, prior to fabricating the bolus, exporting the refined digital bolus model to a treatment planning system to repeat a dose calculation based on the refined digital bolus model.

In another aspect, there is provided a system for modifying a digital bolus model for use in radiation therapy, the system comprising:
control and processing circuitry comprising at least one processors and associated memory, wherein the at least one processor configured to execute instructions stored in the memory for performing the steps of:
identifying a hotspot associated with a digital bolus model, the digital bolus model defining an outer surface and an inner surface, wherein the inner surface is shaped to conformally contact a subject during radiation therapy;
processing the digital bolus model to identify, within the outer surface, a local maximum satisfying search criteria, the search criteria associating the local maximum with generation of the hotspot; and
refining the digital bolus model by modifying a subregion of the outer surface to reduce an intensity of the hotspot, the subregion including the local maximum, thereby obtaining a refined digital bolus model.

In another aspect of the system, the control and processing circuitry is configured such that the local maximum is determined to satisfy the search criteria associated with the hotspot by: determining a hotspot location measure associated with a location of the hotspot and a local maximum location measure associated with a location of the local maximum; determining that the hotspot location measure and the local maximum location measure satisfy proximity criteria.

The control and processing circuitry may be configured such that determining that the hotspot location measure and the local maximum location measure satisfy proximity criteria comprises:
projecting one or both of the hotspot location measure and the local maximum location measure, such that after projection, the hotspot location measure and the local maximum location measure reside within a common two-dimensional region; and
determining that the hotspot location measure and the local maximum location measure satisfy the proximity criteria within the common two-dimensional region.

The control and processing circuitry may be configured such that the local maximum is determined to satisfy the proximity criteria associated with the hotspot by:
projecting the hotspot location measure onto the outer surface, thereby obtaining a projected hotspot location measure; and
determining that the projected hotspot location measure and the local maximum location measure satisfy the proximity criteria.

The control and processing circuitry may be configured such that the local maximum is determined to satisfy the proximity criteria associated with the hotspot by:
projecting the hotspot location measure and the local maximum location measure onto a reference plane that is perpendicular to a beam axis defined by a treatment plan associated with the subject, thereby obtaining a projected hotspot location measure and a projected local maximum location measure; and
determining that the projected hotspot location measure and the projected local maximum location measure satisfy the proximity criteria.

The control and processing circuitry may be configured such that the hotspot location measure is a location of a center of the hotspot and the local maximum location measure is a location of the local maximum, and such that determining that the projected hotspot location measure and the projected local maximum location measure satisfy proximity criteria comprises determining that a projection of the location of the center of the hotspot onto the reference plane and a projection of the location of the local maximum onto the reference plane have a separation less than a separation threshold.

The control and processing circuitry may be configured such that the hotspot location measure is a three-dimensional hotspot margin surrounding the hotspot, and such that determining that the projected hotspot location measure and the projected local maximum location measure satisfy proximity criteria comprises determining that a projection of the three-dimensional hotspot margin onto the reference plane spatially overlaps with a projection of the local maximum location measure onto the reference plane. The control and processing circuitry may be configured such that the local maximum location measure demarcates a peak region surrounding the local maximum, and such that determining that the projected hotspot location measure and the projected local maximum location measure satisfy proximity criteria comprises determining that the projection of the three-dimensional hotspot margin onto the reference plane spatially overlaps with a projection of the peak region surrounding the local maximum. The control and processing circuitry may be configured such that the peak region extends to a valley, such that beyond the valley, a height contour associated with the outer surface does not enclose the local maximum.

In another implementation of the system, the control and processing circuitry is operably connectable to a treatment planning system for obtaining the digital bolus model.

In another aspect, there is provided a method of refining a digital bolus model for use in radiation therapy, the method comprising:
  obtaining a digital bolus model, the digital bolus model defining an outer surface and an inner surface, wherein the inner surface is shaped to conformally contact a subject during radiation therapy;
  identifying a hotspot associated with the digital bolus model; processing the digital bolus model to identify, within the outer surface, a local maximum satisfying search criteria, the search criteria associating the local maximum with generation of the hotspot; and
  refining the digital bolus model by modifying a subregion of the outer surface to reduce an intensity of the hotspot, the subregion including the local maximum, thereby obtaining a refined digital bolus model.

A further understanding of the functional and advantageous aspects of the disclosure can be realized by reference to the following detailed description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments will now be described, by way of example only, with reference to the drawings, in which.

DETAILED DESCRIPTION

Figure 1:
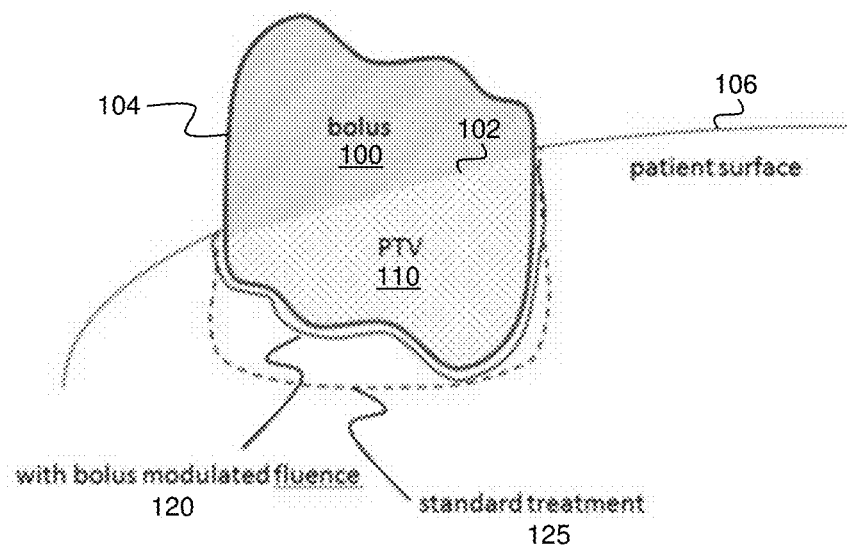
FIG. 1 shows a radiation therapy bolus shaped to modulate an electron beam such that the modulated beam achieves a dose having an improved conformity to the planning target volume (PTV).

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The Use of Custom Radiation Bolus for Improved PTV Coverage

The electron radiation therapy treatment process typically involves the selection of the energy of the electron beam and the aperture dimensions in order to achieve a suitable planning treatment volume (PTV) coverage. The conventional electron radiation therapy planning process does not provide a mechanism for conforming the dose in depth to the distal margin of the PTV. Electron radiation therapy has benefitted from the use of a radiation therapy bolus having an inner patient-contacting surface that has a curvature selected to conformally contact the patient during use and an outer surface that does not contact the patient and has a shape that is configured to modify the incident radiation beam. The curvature of this outer surface is designed to modify the incident radiation beam such that the dose delivered to the patient achieves a desired coverage of the PTV.

An example of such a radiation bolus is shown in FIG. 1, in which an inner surface 102 of the radiation therapy bolus 100 conforms to the surface of the patient 106. The outer surface 104 of the radiation therapy bolus 100 is shaped to modulate the incident radiation beam such that the resulting dose distribution 120 provides a significantly improved overlap of the resulting dose with the PTV 110 when compared to the dose distribution 125 that would have been achieved without the presence of the custom radiation therapy bolus.

Such a custom radiation therapy bolus can be fabricated, for example, using volumetric image data (e.g. computed tomography (CT) image data), acquired prior to radiation therapy, to define the shape of the inner surface of the bolus. With accurate measurements of the patient's skin and body contours, the radiation therapy bolus can be designed to mate accurately to the patient surface, even in the presence of very complex geometries, such as the regions around the face, ears, or surgical cavities. While the patient-facing inner surface of the bolus is shaped based on the body geometry, the outer (non-patient facing) surface of the bolus is shaped so that incident radiation, when applied from one or more points external to the body through the bolus (e.g. defined by a radiation treatment plan), results in a dose distribution (e.g. a 90% isodose contour) that closely conforms to the PTV margin.

While the design of the inner surface of the bolus (the surface mating to the skin of the patient) may be based on volumetric image data (e.g. CT image data), the design of the outer surface of the bolus to target the dose delivered to the PTV is non-trivial. In particular, in the case of electron-based therapy, electrons scatter within any medium in a complex way, and thus simple approaches such as ray-tracing may not be adequate.

Example Method of Design of Custom Radiation Therapy Bolus

Figure 2:
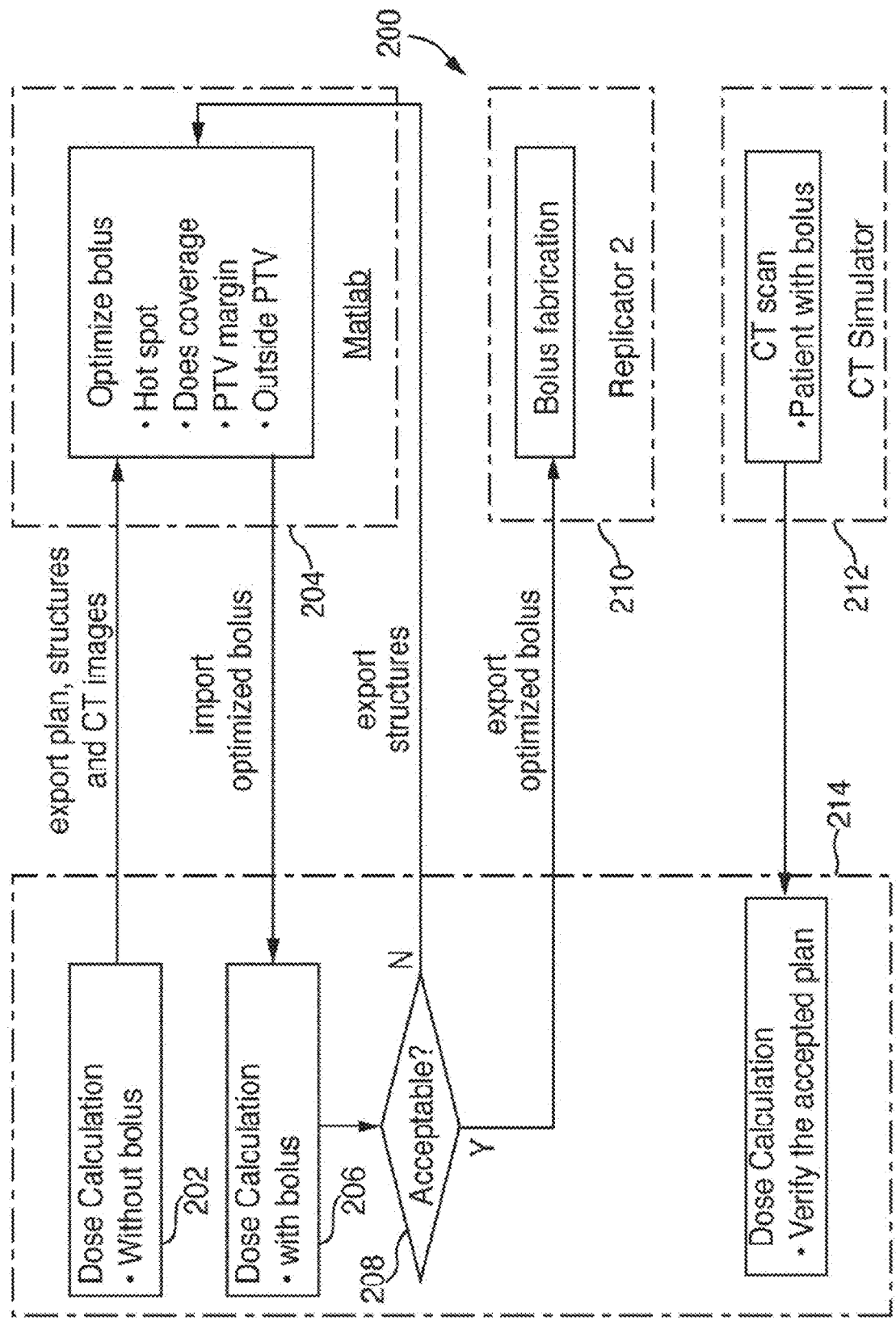
FIG. 2 shows an example of a method for generating a radiation therapy bolus.

US Patent Application No. 2016/0256709, titled "SYSTEM AND METHOD FOR MANUFACTURING BOLUS FOR RADIOTHERAPY USING A THREE-DIMENSIONAL PRINTER" and filed on May 17, 2016, discloses an example method for designing a custom radiation therapy bolus, shown in the flow chart provided in FIG. 2. As shown in the flow chart, after calculating an initial dose distribution in absence of bolus 202, the treatment plan, CT set, structures and dose distribution are provided to a system 204 implementing an example bolus design algorithm. The system 204 calculates an initial approximation of bolus design to achieve conformal coverage of the target volume. The system can provide the bolus design back to the planning system for dose calculation with the bolus design 206. The system can iterate this process in an automated fashion with subsequent cycles also addressing more subtle aspects of improvement of the dose distribution, such as hot-spots, cool spots and optimization of conformity at the edges of the target volume. For example, if the dose calculation with bolus 206 is not acceptable 208, then the system 204 can iterate on the bolus design again. According to the flow chart in FIG. 2, if the bolus design is acceptable 208, then the bolus can be exported, such as via an STL file format, to a bolus fabrication device 210, such as a 3D printer. The example dose calculation 214 can operate according to the electron Monte Carlo (eMC) algorithm but can be replaced with any suitably accurate electron dose calculation algorithm. Similarly, for different types of radiation therapy, different algorithms can be applied, such as an algorithm for proton or photon therapy.

The example bolus optimization and design system of US Patent Application No. 2016/0256709, shown in FIG. 2 of the present application, is modular, i.e. the bolus design portion 204 is isolated from the dose calculation portion 202, 206. For proton therapy, the eMC electron calculation algorithm in the treatment planning system could be replaced by a proton dose calculation algorithm. Example algorithms for proton dose calculation may be analytic or Monte Carlo. Some tuning of the bolus optimization algorithm would be required for use in proton therapy applications, notably the parameters of regional modulation and adjustment at Planning Target Volume margin.

Figure 3:
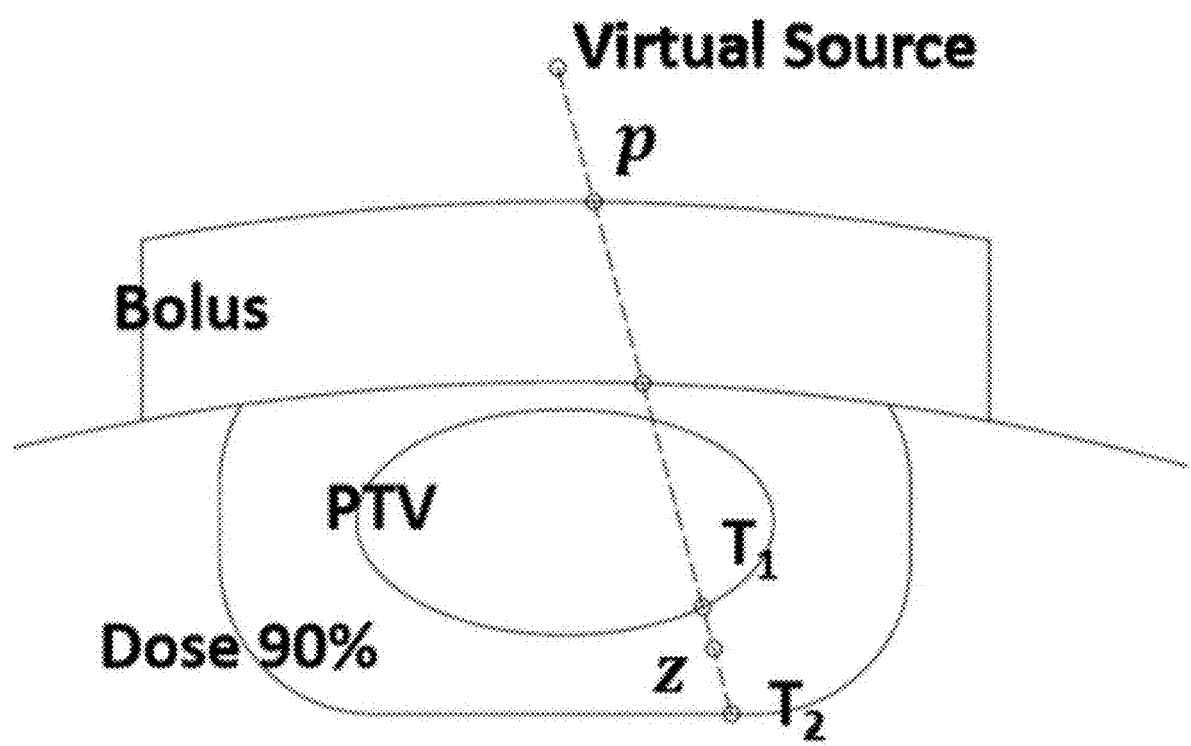
FIG. 3 illustrates example parameters employed when computing a digital bolus model.

FIG. 3 illustrates a non-limiting example of a bolus design calculation described in US Patent Application No. 2016/0256709 (e.g. a calculation performed in system 204 in FIG. 2). The example bolus design method involves a calculation on a grid containing the isocenter and perpendicular to central axis. The bolus thickness is calculated using a grid size of 2.5 mm as default; however a finer grid can be used for improved precision. According to the example method, RT structures exported from a radiation therapy treatment planning system (i.e., 'bolus', 'PTV', 'Dose 90%' and 'Hot Spot' (if required)), are segmented into distal (i.e., deeper) and proximal (i.e., shallower) surfaces according to the maximum and minimum lateral coordinates. Ray lines are traced from the virtual source to each point on the grid and extended to the distal side of PTV and 90% isodose surfaces. For ray lines intersecting the PTV, the distance $z_{real}=T_1-T_2$ is calculated and $z_{real}$ is converted to an effective distance $z_{eff}$ using the coefficient of equivalent thickness (CET) method (since patients typically contain tissue inhomogeneities).

The example method calculates an effective shift of bolus thickness (SBT) for correcting the bolus thickness in a given bolus design iteration. The SBT for a given point p on the grid is given by:

$$SBT_p = \frac{1}{CET(\text{Bolus})} \int_{T_2}^{T_1} CET(z)dz,$$

where CET(z) is the density at point z relative to that of water. Because the initial plan is calculated with no bolus (see 202 in FIG. 2) and the requirement of the example method is complete coverage of the PTV by the 90% dose surface, all $SBT_p$ values will be positive in the first iteration. In subsequent iterations, $SBT_p$ values are employed to adjust the design of the bolus relative to the shape of the outer surface of the bolus relative to that employed in the previous iteration (or relative to an initial bolus design). In the present example, the density is obtained from the HU to density lookup table in the planning system which, in turn, may be obtained during eMC commissioning from a HU calibration phantom. Each iteration of the algorithm includes calculation by the eMC algorithm such that subsequent modifications are based on an accurate dose distribution.

FIGS. 4A-4F illustrate a schematic representation of a bolus design modification algorithm, according to the example calculation method of US Patent Application No. 2016/0256709. The lines marked with "X" indicate the previous iteration's bolus (which may be an initial bolus design for the first iteration) and corresponding 90% isodose line which does not yet conform well to the PTV (lines marked with "+") in this example. The lines marked with "*" show the bolus shape modified by the current step (FIGS. 4A-4F) (i.e., change in thickness by SBT value or a regional modulation operator), as well as the effect of this change on the dose distribution. For reference, lines marked with "=" in FIGS. 4B to 4F denote the bolus shape and 90% isodose line from the previous step. Hot spots are indicated as circles. The individual steps are: (FIG. 4A) estimation of the bolus thickness based on SBT values, (FIG. 4B) smoothing for hot spots, (FIG. 4C) smoothing for dose coverage, (FIG. 4D) smoothing for surface irregularity, (FIG. 4E) adjustment at PTV margin and (FIG. 4F) extension outside PTV.

Figure 5:
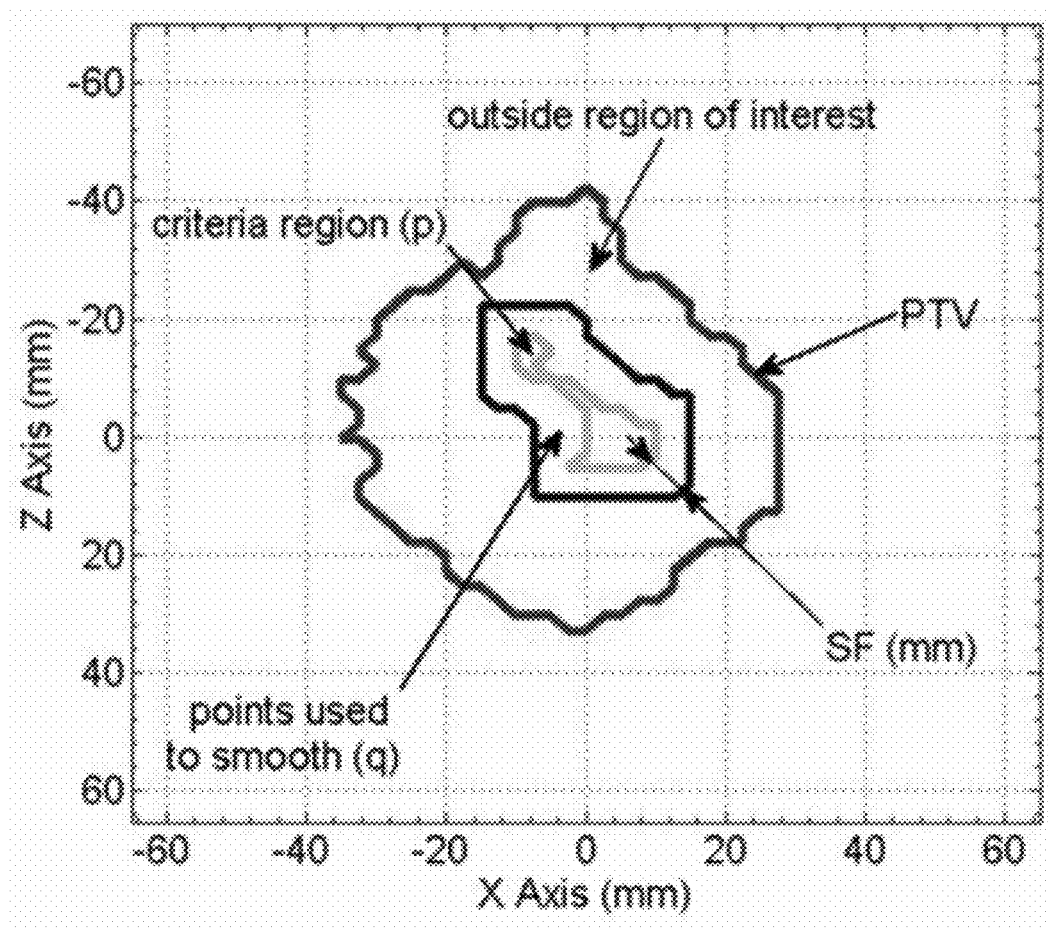
FIG. 5 shows an example of the boundaries that may be employed when performing hot spot smoothing.

While the calculation of SBT values largely improves conformity of the 90% isodose surface, it does not address secondary effects, such as regional hot or cold spots or the effect of irregular bolus surface. Separate regional modulation operators are described in US Patent Application No. 2016/0256709 to address: i) hot spots in the PTV, ii) undercoverage, iii) irregular bolus surface, iv) coverage at the PTV margin, and v) extension of the bolus beyond the PTV. These operators may be applied sequentially; however, the dose calculation may be performed by the treatment planning system. Three of the operators (namely operators i-iii noted above) involve regional smoothing. In these cases, the SBT matrix is segmented into regions of interest containing points p where modulation is required, neighboring points q that are used to smooth p, and points outside of the region of interest, as shown in FIG. 5. The following smoothing operators are used according to the application:

$$SBT_p = \begin{cases} RM(p, q, SF, \text{Mode1}) = \dfrac{0 + \sum_{r_{pq}<SF} SBT_q \exp(-r_{pq}^2/2SF^2)}{1 + \sum_{r_{pq}<SF} \exp(-r_{pq}^2/2SF^2)} \\[2ex] RM(p, q, SF, \text{Mode2}) = \dfrac{SBT_p + \sum_{r_{pq}<SF} SBT_q \exp(-r_{pq}^2/2SF^2)}{1 + \sum_{r_{pq}<SF} \exp(-r_{pq}^2/2SF^2)} \end{cases}$$

where $r_{pq}$ is the distance between p and q, and SF(mm) is the smoothing factor, controlling the width of smoothing region and smooth level (i.e., 5, 10, and 20 mm for low, medium, and high).

FIG. 5 is a schematic representation of regions involved in smoothing (e.g., to alleviate a hot spot) according to the example method disclosed in US Patent Application No. 2016/0256709. The thick outer line shows the projection of the PTV onto a calculation plane perpendicular to the beam axis. The inner line denotes the region of interest satisfying the hot spot criterion and containing points, p, that will be adjusted. Points q between the middle and inner lines are included in the smoothing operation but are not adjusted.

Figure 4A:
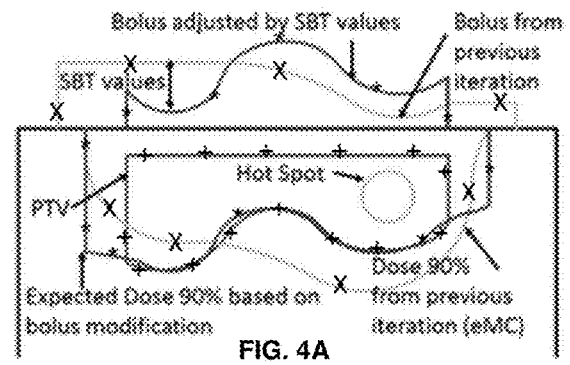
FIGS. 4A-4F illustrates an example method for modifying a digital bolus model.
Figure 4B:
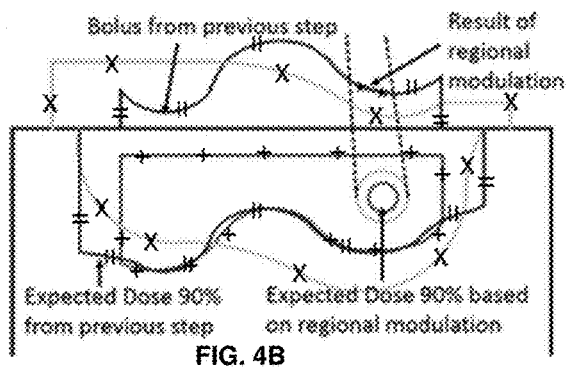

Smoothing for hot spot reduction is performed as follows according to the example method taught in US Patent Application No. 2016/0256709. The first modulation operator aims to alleviate the hot spots that exist within the distribution after the previous iteration of eMC dose calculation (e.g. as shown in FIG. 4B). No smoothing is required if maximum dose is less than 110% of the prescription dose; otherwise, the hot spot region is projected to the SBT plane and smoothed. RM (Mode 1) is chosen since the original SBT value in this criteria region may differ appreciably compared to the surroundings.

Figure 4C:
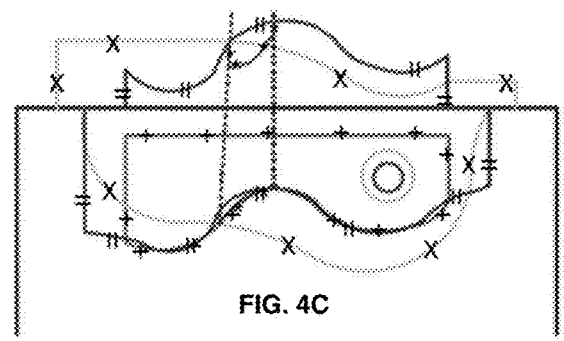

Smoothing for dose coverage is performed as follows according to the example method taught in US Patent Application No. 2016/0256709. Although the calculation of SBT values aims to provide full coverage by the 90% isodose surface, accurate eMC calculation following bolus design may reveal undercoverage in certain regions of the PTV. In these regions, SBT values will be negative (i.e., to decrease bolus thickness). However, testing of the effect of SBT adjustment alone reveals that the bolus thinning must be extended somewhat beyond the region defined by the projection of the under dosed area. Accordingly, negative SBT values in the region of interest are retained, while surrounding values are smoothed (e.g. as shown in FIG. 4C). RM (Mode 2) is invoked, which will always increase target coverage since all affected points assume negative values following the operation.

Figure 4D:
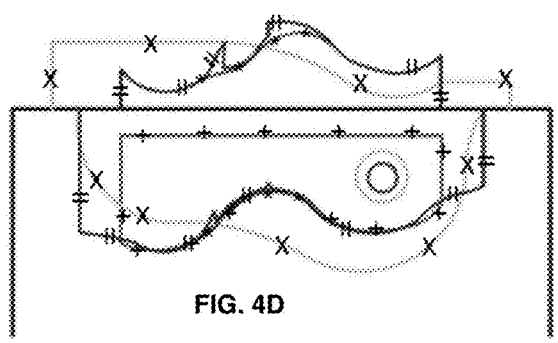

Smoothing for potential irregular surface is performed as follows according to the example method taught in US Patent Application No. 2016/0256709. Following the previous operations, discontinuities may be present at the boundaries of regions of interest. Surface irregularities are identified by using a gradient threshold criterion equal to two times of the mean value of gradient magnitude, and smoothed using RM (Mode 2) (e.g. as shown in FIG. 4D).

Figure 4E:
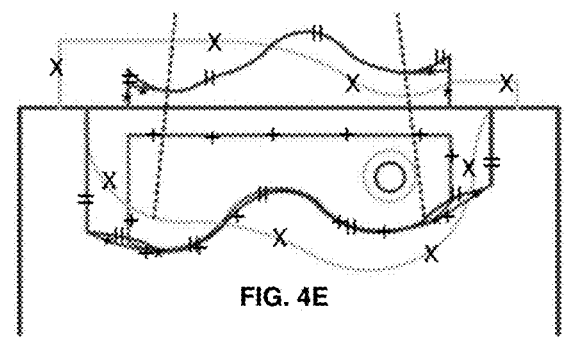

Adjustment at PTV margin is performed as follows according to the example method taught in US Patent Application No. 2016/0256709. Relative to more central regions, the edge of the PTV receives less scattered radiation dose simply due to collimation by the electron applicator. To remedy underdosing in this region, a region of interest is defined as a 10 mm wide border inside of the projection of the PTV onto the SBT matrix (e.g. as shown in FIG. 4E). A function is applied to reduce bolus thickness according to:

$$SBT_p = \begin{cases} SBT_p \times (1 - KerfMA(\max(K1 - r_{pm}, 0))), & \text{if } SBT_p > 0 \\ SBT_p \times (1 + KerfMA(\max(K1 - r_{pm}, 0))), & \text{if } SBT_p < 0 \end{cases}$$

where values are adjusted along radial lines from the central axis: m exists on the inner boundary of the region of interest, p exists within the region of interest, $r_{pm}$ is the distance between p and m, and where $$KerfMA(x) = \exp\left(-\frac{x^2}{2\text{sigma}^2}\right)$$

and $$K1 = \sqrt{-2 \ln(0.01)\text{sigma}^2}$$

(i.e., the distance over which KerfMA(x) increases from 0.01 to 1). In practice, effective values of sigma were determined to be related to beam profile, increasing with both energy and applicator dimension. An approximation of $$\text{sigma} = \sqrt{\text{Energy} \times \text{Applicator}}$$

was employed.

Figure 4F:
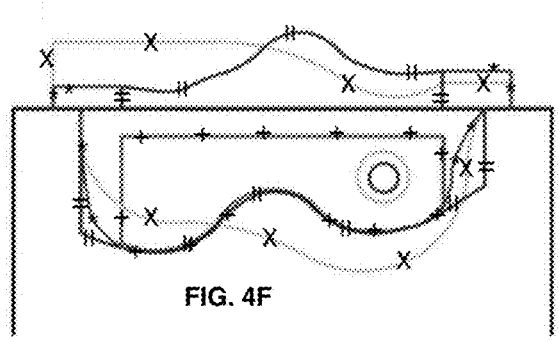

Shift outside PTV is performed as follows according to the example method taught in US Patent Application No. 2016/0256709. The area corresponding to all ray lines between the edge of the PTV and a distance 1.0 cm beyond the electron aperture are subject to this operator. In this region, bolus thicknesses are simply extruded:

$$SBT_p = SBT_n$$

where n is the intersection of PTV contour and line from p to the projection of central axis (e.g. as shown in FIG. 4F).

Improved Hot Spot Reduction Method

The example bolus design method of US Patent Application No. 2016/0256709, as described above and illustrated in FIGS. 1-5, has been successfully employed for the design and manufacture of multiple custom radiation bolus. However, the present inventors have found that in some cases, when the hot spot reduction method described above is employed, hot spots may persist in the calculated dose after performing the hot spot reduction step. In particular, the present inventors found that the ability to perform a suitable hot spot correction using the smoothing method described above dependent on the specific surface shape of a given electron radiation treatment bolus.

The present inventors noted that in some cases, even after applying the hot spot smoothing step described above, significant inhomogeneities would remain in the modified bolus as a result of an additional scattering component of the primary beam. The present inventors, in seeking to develop an understanding of why some hot spots would persist even after performing the hot spot correction step, realized that hot spots can be generated due to the scattering of the primary radiation beam by one or more peaks (local maxima) in the outer surface of the bolus.

Figure 6:
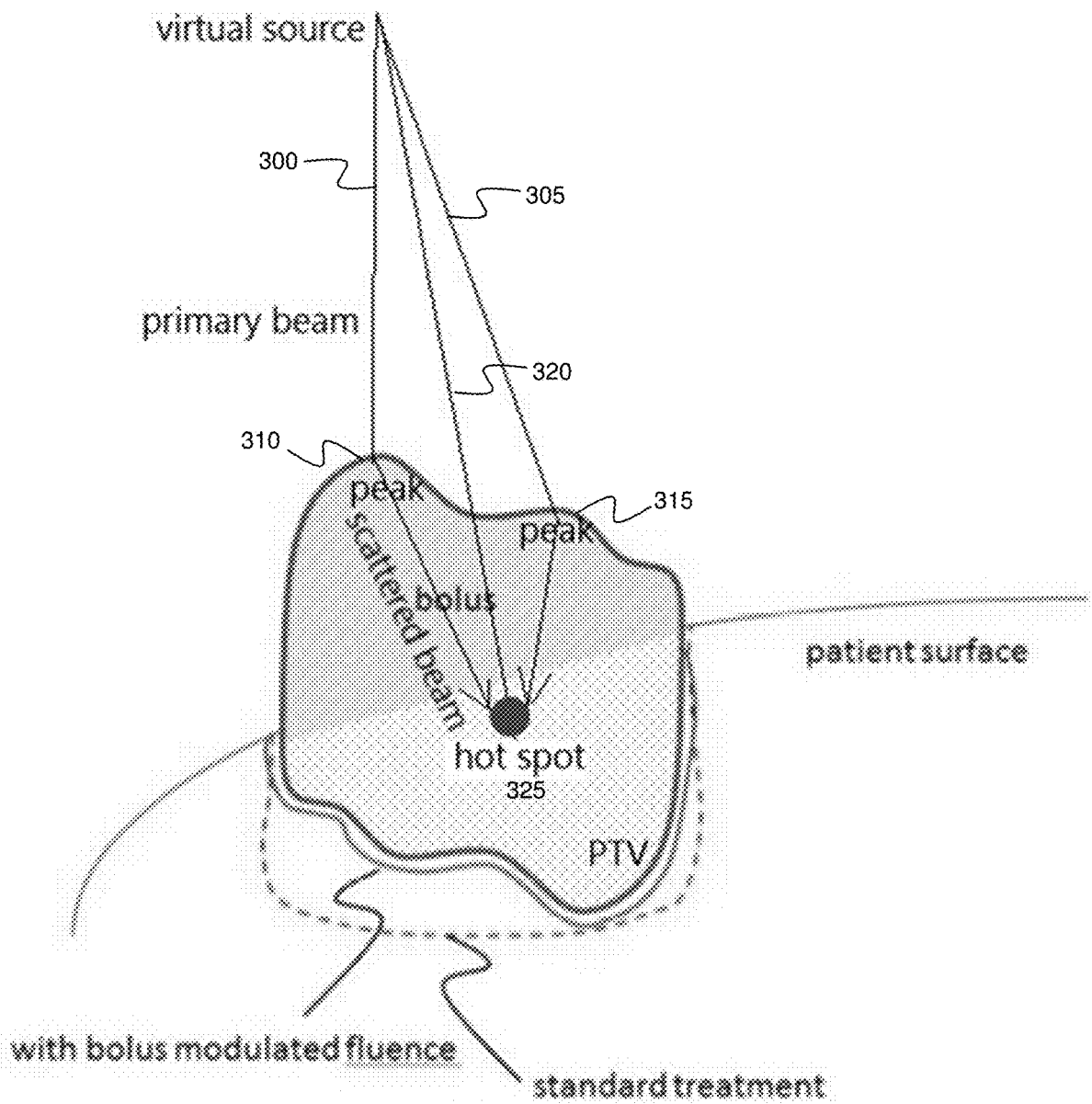
FIG. 6 illustrates the role of peaks in the outer surface of a bolus in generating a hot spot.

This effect is shown in FIG. 6, which schematically illustrates the effect of peaks in the outer surface of the bolus on the redirection of the incident radiation and the resulting generation of a hot spot within the PTV. Radiation rays 300 and 305 are incident on the peak regions 310 and 315 and are scattered toward a common region within the PTV. Ray 320, which passes through a valley between the two peaks, does not scatter significantly and also passes through the common region. The effective focusing of these scattered rays by the outer surface of the bolus generates the hot spot 325.

Accordingly, as shown in FIG. 6, depending on the beam energy, aperture of the treatment field, optimization characteristics of the plan, bolus material properties and shape of the modulated bolus, a hot spot may arise in the PTV due to the scattered component of electron radiation originating from one or more peaks. This scattered component of the incident radiation is added to other incident radiation rays, such as the unscattered or weakly scattered beam portion that passes through a valley adjacent to a peak. Since beam energy, field aperture, optimization of the plan and bolus material are all pre-set for a particular treatment plan and are unlikely to be changed, the shape of the bolus (e.g. peak-to-valley ratio of the modulated surface of the bolus) represents the feature in the treatment plan that may be further optimized for the reduction of hot spots in Modulated Electron Radiation Therapy (MERT) treatment plans.

The present inventors, having established a link between peaks in the outer surface of the bolus and the generation of hot spots, set out to improve or replace the aforementioned hot spot correction algorithm with a more robust and effective algorithm. The aforementioned hot spot reduction algorithm described in US Patent Application No. 2016/0256709 does not consider the features in the outer surface of the bolus that generate the hot spot. This previous hot spot reduction method, described above with reference to FIG. 5, merely involves projecting the hot spot criteria (e.g. hot spot margin) onto a plane and smoothing the bolus within a region of the outer surface that corresponds to this projection, where the smoothing is based on peripheral points beyond the projected hot spot region, without any consideration of the curvature of the outer surface. This method is therefore agnostic with regard to any peaks that may be present in the outer surface of the bolus. For example, referring to FIG. 6, this previous hot spot correction algorithm would "miss" the two peaks 310 and 315 and only smooth the outer surface of the bolus within the valley region, leaving the two peaks substantially intact, without achieving a significant reduction in the hot spot generated by the presence of the peaks. The present inventors therefore determined that a more robust and effective algorithm would need to involve aspects including (i) identifying of a peak responsible for the generation of a hot spot, and (ii) smoothing of the outer surface of the bolus in a region including the identified peak.

A non-limiting example embodiment of a method of refining a digital bolus model to reduce hot spots based on peak identification is described as follows with reference to FIGS. 7A-7E. In brief, the present example method involves the identification of at least one hot spot and at least one local maximum (i.e. peak) in the outer surface of the digital bolus model (i.e. at least one peak in the outer surface of the bolus). Proximity criteria is then evaluated to determine whether or not a given local maximum is associated with a given hot spot, such that when the proximity criteria is satisfied, the hot spot is likely generated, at least in part, due to beam scattering effects arising from the presence of the given local maximum. The digital bolus model is then modified by smoothing the digital bolus model within a region surrounding each local maximum that is found to be associated with a given hot spot, such that the hot spot intensity is reduced.

In an initial step of the example method illustrated in FIGS. 7A-7E, one or more hot spots associated with a digital bolus model are identified. A hot spot may be identified, for example, via a dose calculation performed by a treatment planning system. In such a case, a hot spot may be exported from the treatment planning system, for example, as an RT structure. For example, in a treatment planning system, hot spot regions (e.g. identified by an RT planner) may be converted into RT structures, so there is a clear visible boundary of the hot-spots on DICOM CT images of the patient. In some example implementations, the hot spot volumes may be outlined using the hot spot RT structure information defined by a treatment planning system, and the hot spot outlines may then be projected onto the beam-eye-view. In another example implementation, a hot spot may be identified based on processing dose distribution data obtained from a treatment planning system. In yet another example implementation, a hot spot may be identified by performing a dose calculation (e.g. a pencil beam calculation).

Figure 7A:
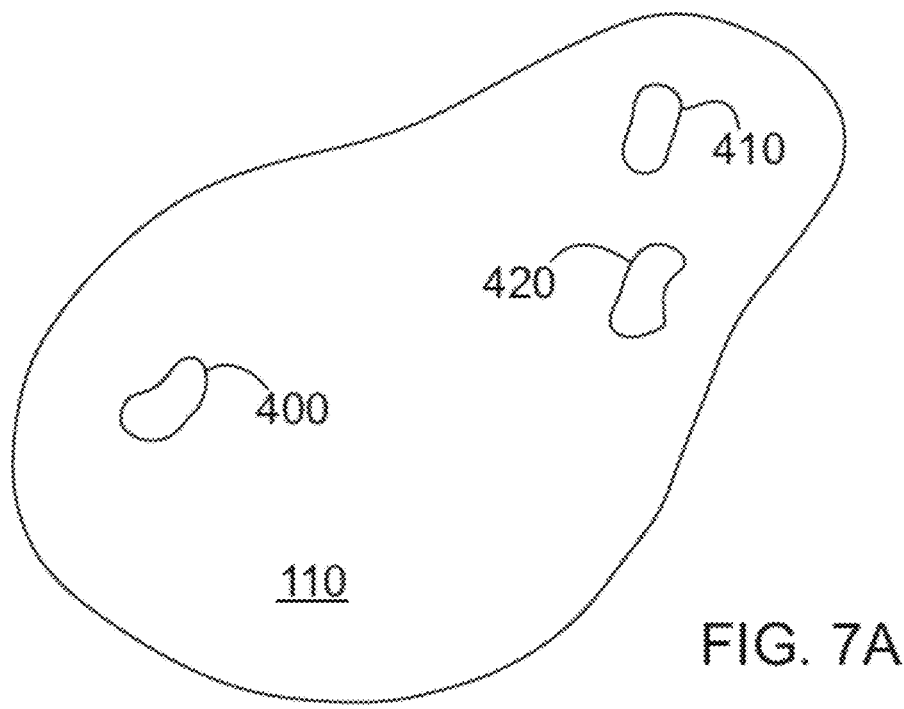
FIGS. 7A-7E illustrate an example method of modifying a digital bolus model to reduce the intensity of a hot spot, where the method is based on the identification and smoothing of one more peaks associated with the hot spot.

FIG. 7A shows contours (e.g. isodose contours) associated with three hot spots (400, 410 and 420), where the contours are projected onto a reference plane that is perpendicular to the beam axis. The beam axis may be determined, for example, based on a treatment plan (e.g. RT plan data obtained from a treatment planning system). In one example implementation, the reference plane may be defined as the plane that tangentially contacts the patient and resides perpendicular to the beam axis. FIG. 7A also shows the projection of the PVT 110 onto the reference plane.

Figure 7B:
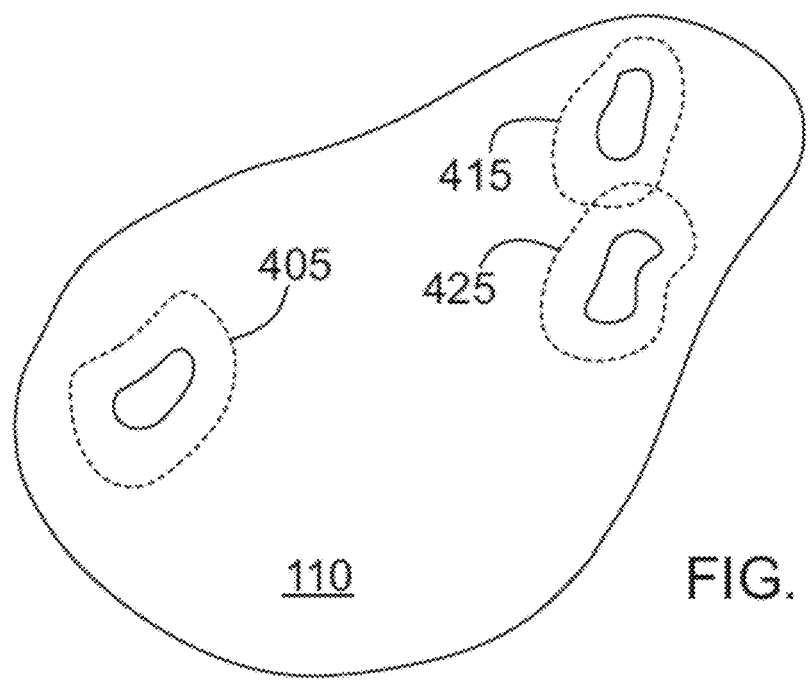

As shown in FIG. 7B, hot spot search margins (405, 415 and 425) may be defined surrounding each hot spot. Such search margins may be employed to associate a peak with a hot spot as explained further below. For example, the outline of a hot spot volume may be scaled to create a search area. This search area may be an equidistant margin around a hot spot (e.g. around a given isodose contour associated with the hot spot; optionally projected to the beam-eye-view). For example, a hot spot search margin surrounding a given hot spot may be defined in the reference plane based on a prescribed distance surrounding the given hot spot (i.e. surrounding a given isodose curve associated with the hot spot) within the reference plane. Alternatively, a hot spot search margin surrounding a given hot spot may be defined three-dimensionally, with a prescribed equal distance surrounding the given hot spot in three dimensions, and the three-dimensional hot spot search margin may be projected onto the reference plane. The hot spot search margin may be user-defined and received as input from a user.

Figure 7C:
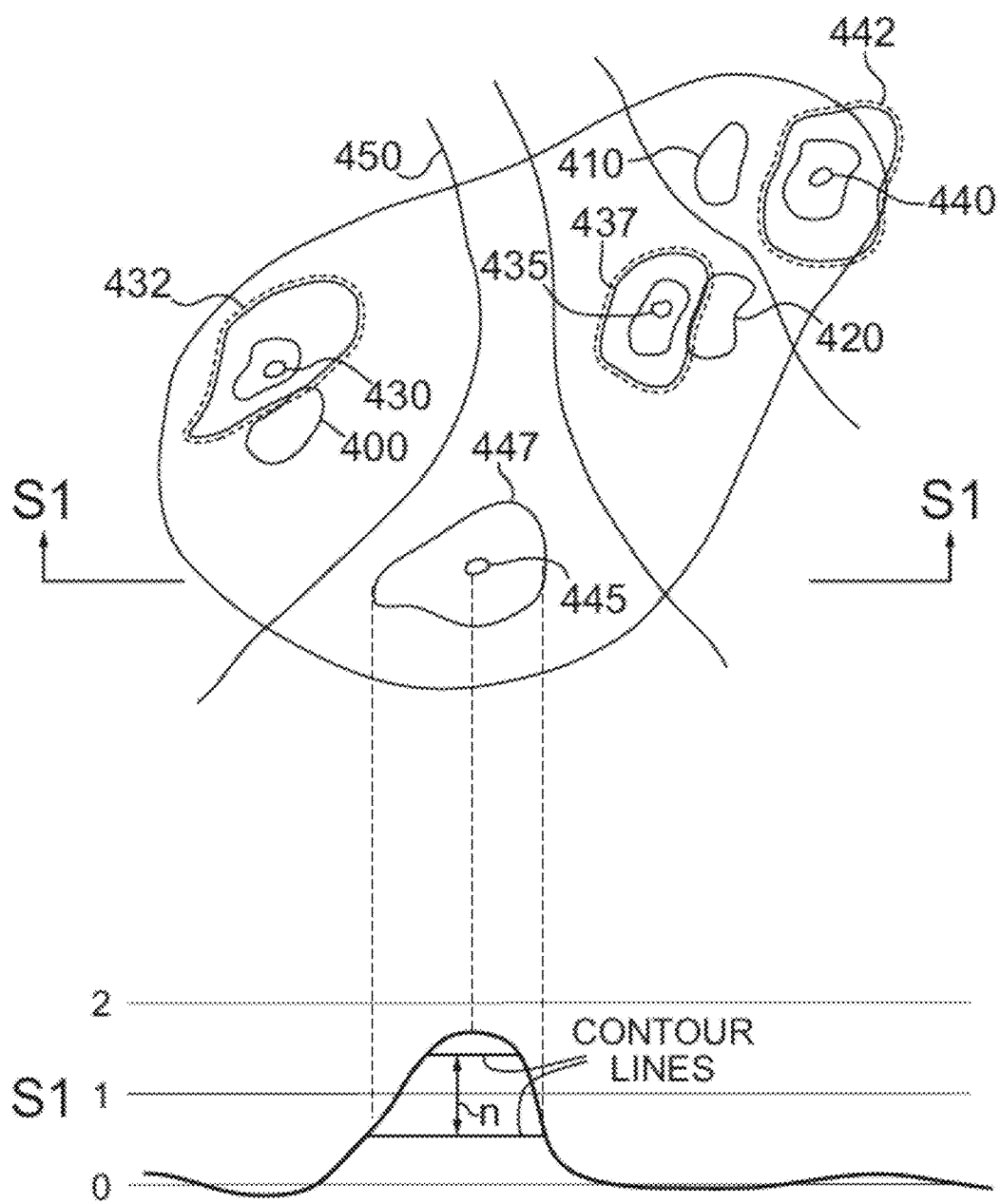

The digital bolus model is then processed to identify the location of one or more local maxima in the outer surface. FIG. 7C shows one example method for identifying peaks in the outer surface of the digital bolus model. As shown in the figure, a topographical representation of the model may be generated by constructing a set of contours defined relative to a plane that is perpendicular to the beam axis (e.g. using the intersection of a set of parallel planes, each orthogonal to the beam axis, with the digital bolus model, thereby generating a heightfield map of the bolus). The contours may be generated relative to the same plane as the reference plane described above. The central point within one or more closed contours may be employed to define the location of a given peak, as shown in FIG. 7C.

It will be understood that a given local maximum (peak) may be identified according to any of several different known peak-finding methods. For example, a peak may be found by finding contours with no inner contours and/or identifying an immediately adjacent contour height of less than unity. In some example implementations, a three-dimensional (e.g. mesh) digital representation of the bolus model may be processed to find the local maxima. Such a method need not be performed by defining a surface height in a directional parallel to the beam axis. In another example implementation, a peak in the outer surface of the digital bolus model may be identified by using slices (planes) parallel to the beam axis. Such slices would provide a contour of the bolus similar to a "2D mountain" in which a peak (local maximum) would be found on a slice after which the height of this 2D mountain is no longer increasing. For example, the starting position for slice generation could be the center of the hot spot, from which a slice plane parallel to the beam axis would move left and right from the center, searching for peaks.

FIG. 7C shows the projection of the location of local maxima 430, 435, 440 and 445 onto the reference plane, along with the projection of the hot spots 400, 410 and 420. It can be seen from the figure that some of the peaks appear to be associated with the formation of the hot spots based on their proximity to the hot spots. Also shown in the figure are base contours 432, 437, 442 and 447 respectively associated with local maxima 430, 435, 440 and 445. The base contour associated with a given peak is shown in the figure as the final outer closed contour surrounding the given peak, beyond which the contours no longer enclose the peak. A base can be found, for example, using a contour-based method, or by processing a three-dimensional digital model to find a location beyond a peak where the bolus slope changes sign. The base contour identifies a valley adjacent to a given peak. It is noted that FIG. 7C also shows a set of contours 450 associated with the patient surface for clarity. The bottom portion of FIG. 7C shows a peak that is characterized by a set of discrete contour lines.

Figure 7D:
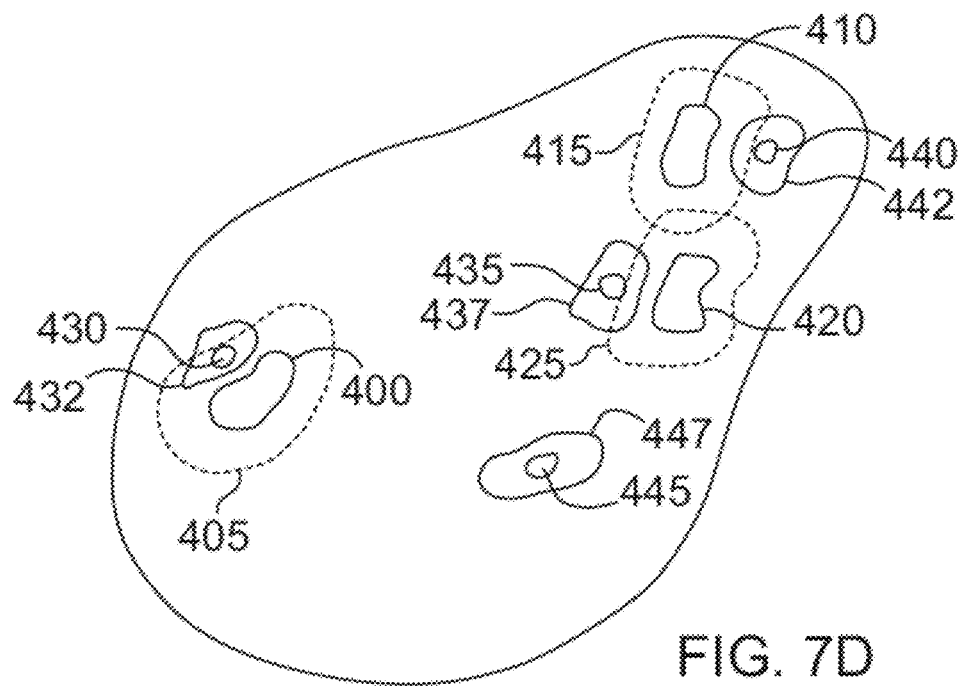
Figure 7E:
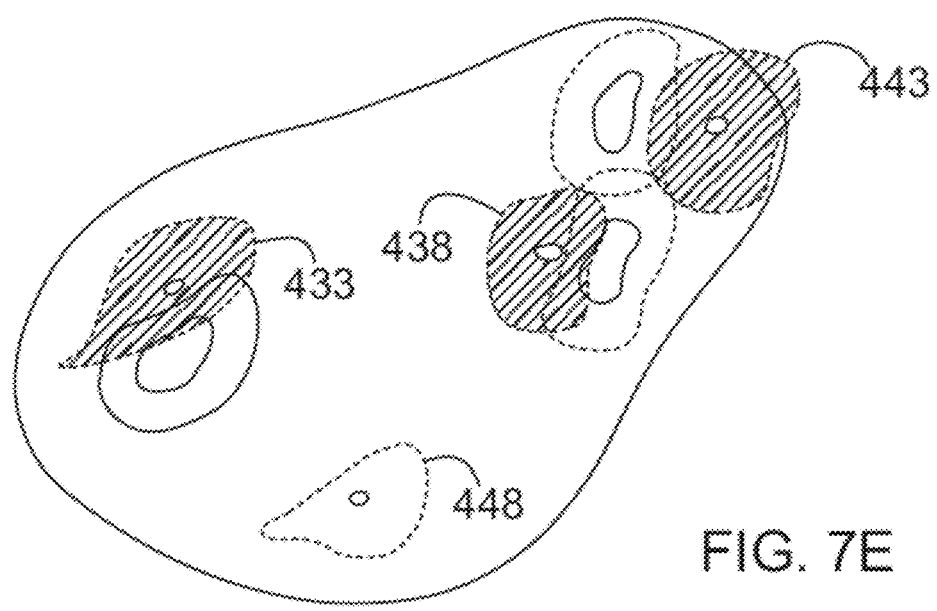

According to the present example method, a local maximum is deemed to be associated with the generation of a hot spot when spatial overlap exists between the projected hot spot search margin and the projected base contour. For example, as shown in FIG. 7D, since base 432 spatially overlaps with hot spot search margin 405, it is deemed that peak 430 is associated with hot spot 400, and a region of the outer surface surrounding peak 430 (e.g. region 433 shown in FIG. 7E) is smoothed to reduce the peak height and thereby reduce the intensity of the hot spot 400 associated with the peak 430. Similarly, since base 442 spatially overlaps with hot spot search margin 415, it is deemed that peak 440 is associated with hot spot 410, and a region of the outer surface surrounding peak 440 (e.g. region 443 shown in FIG. 7E) is smoothed to reduce the peak height and thereby reduce the intensity of the hot spot 410 associated with the peak 440. Furthermore, since base 437 spatially overlaps with hot spot search margin 425, it is deemed that peak 435 is associated with hot spot 420, and a region of the outer surface surrounding peak 435 (e.g. region 438 shown in FIG. 7E) is smoothed to reduce the peak height and thereby reduce the intensity of the hot spot 420 associated with the peak 435. However, since base 447 does not spatially overlaps with any hot spot search margin, it is deemed that peak 445 is not associated with any hot spot, and a region of the outer surface corresponding to peak 445 is not smoothed. In some example implementations, for a given peak that is associated with a hot spot, the region surrounding the peak to be modified (smoothed) may, for example, be associated with a projection that is bounded by a base contour associated with the peak, lie within the base contour, or extend beyond the base contour (e.g. modification regions 433, 438 and 443 extend beyond their respective associated base contours, as can be seen comparing FIG. 7D and FIG. 7E).

According to the present example method, the modification that is applied to the region surrounding the peak (and including the peak) may including a scaling of the height of the outer surface. The scaling may increase from the outer perimeter of the modified region towards the peak, so that the maximum scaling occurs at the peak. The scaling may be based, for example, on a linear or non-linear function. The scaling function or factor that is applied to modify the outer surface within the region surrounding the peak may depend on the ratio of the height of the peak to the height of a valley adjacent to the peak.

One or more parameters of a scaling factor or function that is employed to modify the outer surface within the region surrounding the peak may be user-configurable. By increasing the scaling factor, the peak is reduced further and further. In one example implementation, the outer surface of the digital bolus model is not modified in the valleys between peaks, but rather, the peaks alone. Depending on the chosen peak-to-valley ratio, reduced peaks are expected to yield less scattered radiation towards the existing hot spot, thus lowering the maximum dose in these regions in the RT plan.

As noted above, the present example method, and variations thereof described below, employ an association between a peak in the outer surface of the bolus and a hot spot to judiciously smooth the bolus in regions associated with the formation of the hot spot via scattering. Since these methods directly address a root cause of hot spot generation, they are expected to provide a significant improvement over conventional hot spot reduction methods.

Figure 8:
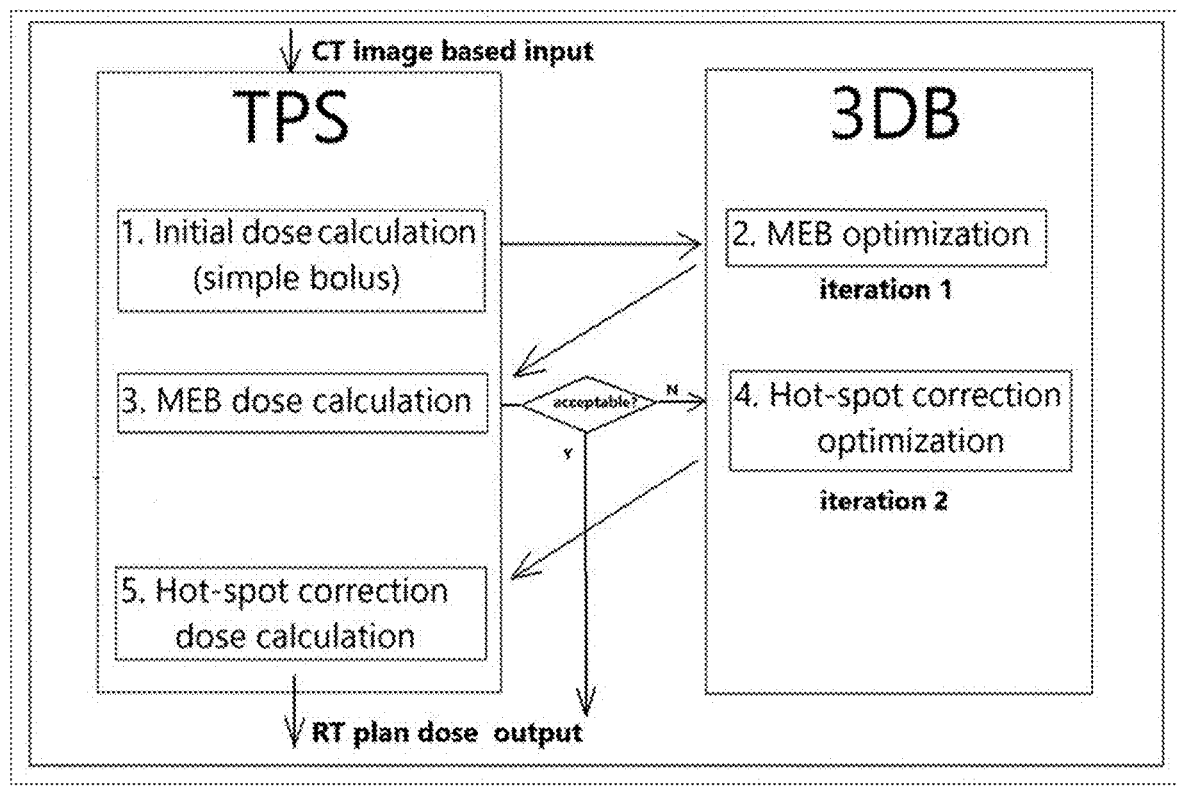
FIG. 8 illustrates an example bolus design and modification workflow.

Referring now to FIG. 8, a flow chart is provided that illustrates an example method of designing and fabricating a radiation therapy bolus. In step 1, a treatment planning system is employed to perform an initial dose calculation. This initial dose calculation may be made in the absence of a digital model bolus model, or using an initial ("simple") bolus model, as shown in the figure. For example, an initial electron RT plan may be made using a uniform thickness (simple) bolus and exported DICOM CT images.

In step 2, an initial iteration of involving the calculation of the digital bolus model (e.g. a modulated electron bolus (MEB) is performed, as shown in the figure) using the results from dose calculations performed by the treatment planning system in step 1. For example, The RT structures, RT dose and RT plan may be obtained and processed, for example, using the bolus modification operators described above, or other bolus design or modification operators known to the skilled artisan.

As shown in step 3, the resulting digital bolus model is then provided (e.g. exported as an RT structure) to the treatment planning system and a subsequent dose calculation is performed.

When the updated dose calculation is deemed to exhibit hot spots (e.g. hot spots that fail to meet acceptance criteria), the digital bolus model is refined using the methods described herein, or variations thereof, as shown in step 4 (e.g. based on the updated RT dose and RT structures obtained from the treatment planning system). The digital bolus model is processed to identify one or more local maxima (peaks) associated with a given hot spot and the outer surface of the bolus is modified within regions surrounding the local maxima that are deemed to be associated with hot spot generation (e.g. according to proximity criteria, as described above).

The resulting refined digital bolus model with reduced associated hot spot intensity may then be provided to the treatment planning system for the calculation of an updated dose (e.g. exported to the treatment planning system as an RT structure), as shown in step 5, resulting in the output of the RT dose and RT plan based on the refined digital bolus model. The refined bolus model is then employed to fabricate the bolus for use in the radiation therapy procedure, for example, using 3D printing or another fabrication process, as described further below.

Figure 9:
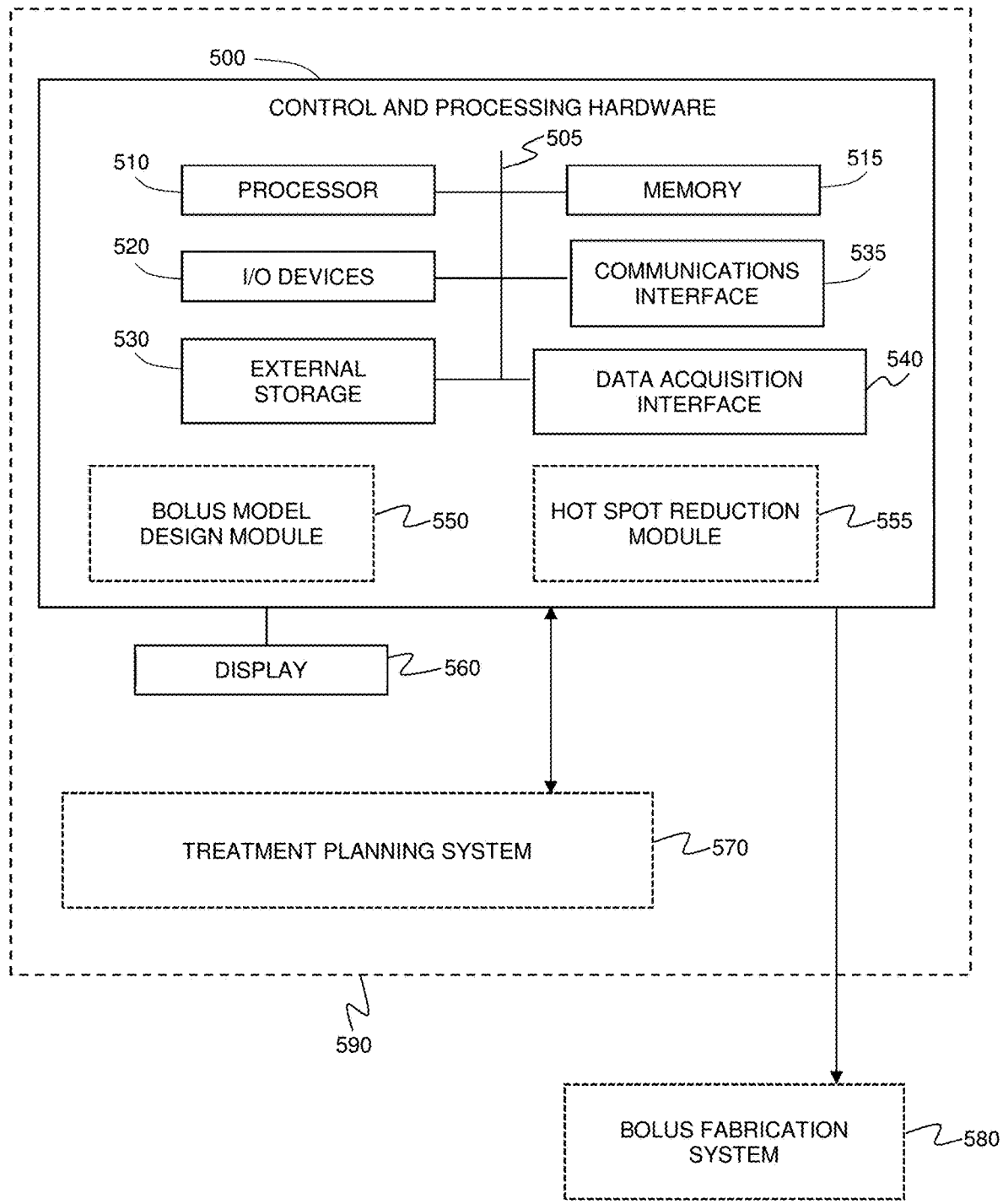
FIG. 9 is a schematic of an example system for designing and modifying a radiation bolus model.

Referring now to FIG. 9, an example system is shown for performing digital bolus design. Control and processing hardware 500 is integrated with or connectable to a treatment planning system 570, and performs digital bolus design and may include a processor 510, a memory 515, a system bus 505, one or more input/output devices 520, and a plurality of optional additional devices such as communications interface 535, display 525, external storage 530, and data acquisition interface 540. In one example implementation, the display 560 may be employed to provide a user interface for displaying images of the digital bolus model and/or for facilitating input to control the operation of the system 500. As shown in FIG. 9, the display and/or the treatment planning system 570 may be directly integrated into a control and processing device, as shown at 590 (for example, as an embedded display), or may be provided as an external device (for example, an external monitor). The control and processing system 500 may be connected to a bolus fabrication system (such as, but not limited to, a 3D printer) for fabricating a bolus.

The methods described herein, including the initial design of the digital bolus model and the refinement of the digital bolus model for hotspot reduction, can be implemented via processor 510 and/or memory 515. As shown in FIG. 9, executable instructions represented as bolus model design model 550 and hot spot reduction module 555 are processed by control and processing hardware 500 to generate an initial digital bolus model and refine the digital bolus model for hot spot reduction based on peak identification, respectively. Such executable instructions may be stored, for example, in the memory 515 and/or other internal storage. The control and processing hardware 500 may be interfaced with a treatment planning system 570, for example, to facilitate the performing of dose calculations and the exporting of relevant RT DICOM elements, including RT dose, RT plan data, and RT structures, as described above.

The methods described herein can be partially implemented via hardware logic in processor 510 and partially using the instructions stored in memory 515. Some embodiments may be implemented using processor 510 without additional instructions stored in memory 515. Some embodiments are implemented using the instructions stored in memory 515 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 500 may be provided as an external component that is interfaced to a processing device. Furthermore, although the bus 505 is depicted as a single connection between all of the components, it will be appreciated that the bus 505 may represent one or more circuits, devices or communication channels which link two or more of the components. For example, the bus 505 may include a motherboard. The control and processing hardware 500 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

It will be understood that the example bolus design workflow and system described with reference to FIGS. 8 and 9 is intended to provide a non-limiting example embodiment. The workflow and/or system may be modified or adapted without departing from the intended scope of the present disclosure. For example, while the example workflow and system involves the use of a treatment planning system and a separate bolus design system, these two systems may be integrated into a common system for integrated processing of the dose calculation and bolus design, as shown by 590 in FIG. 9.

A custom bolus can be manufactured according to many different example methods and is particularly well-suited to automated fabrication methods such as 3D printing. 3D printing provides several advantages over manual approach to bolus fabrication. 3D printing is a specific form of additive manufacturing. One of the most common methods of 3D printing is fused deposition modeling (FDM). This process has recently has become widely accessible at low cost, such as MakerBot devices. 3D printing involves a fabrication process that uses a CAD model as input to create a 3D physical model by applying many successive layers of the chosen material at a high resolution, such as a resolution of 100 micrometers, although the system can use other resolutions and capabilities.

Using 3D printing, bolus fabrication can be largely automated, and the precision can be substantially improved relative to manual approaches. Moreover, because the fabrication is automated, human error is reduced. Thus, 3D printed bolus can provide improved conformity between bolus and patient surface, reducing the possibility of air cavities which would degrade accuracy of treatment or would provide a dosage above or below what is desired. For example, a custom radiation therapy bolus formed from PLA (polylactic acid) is durable, unlike traditional wax bolus materials. Increased durability can be particularly important for treatment regimes with the bolus over an extended period of time, such as a regime of 30 daily treatments. A precisely generated bolus can provide a customized, highly conformal dose distribution for each individual patient based on his or her specific needs and situation. 3D printing allows for a clinic or doctor to fabricate optimized bolus designs in-house rather than placing an order to an off-site service which may be expensive or require a lengthy wait. 3D printing can provide a cost reduction, time savings, improved treatment flexibility, and ability to respond to changing clinical demands by modifying the bolus design during the course of the treatment.

Referring again to FIGS. 7A-7E, it will be understood that the example method of peak-based bolus modification for hot spot reduction is intended to illustrate but one example method. Various alternative embodiments and adaptations are considered below, with reference to FIG. 10, which discloses a general method of peak-based bolus modification for hot spot reduction. In step 600, a digital bolus model is obtained, where the digital bolus model defines an outer surface and an inner surface of the bolus, where the inner surface is shaped to conformally contact a subject during radiation therapy. The digital bolus model may be generated, for example, according to the example methods described above, such as according to the methods represented by block 204 in FIG. 2 and in FIGS. 4A-4F. It will be understood, however, any suitable method of generating an initial bolus digital model may be employed.

Figure 10:
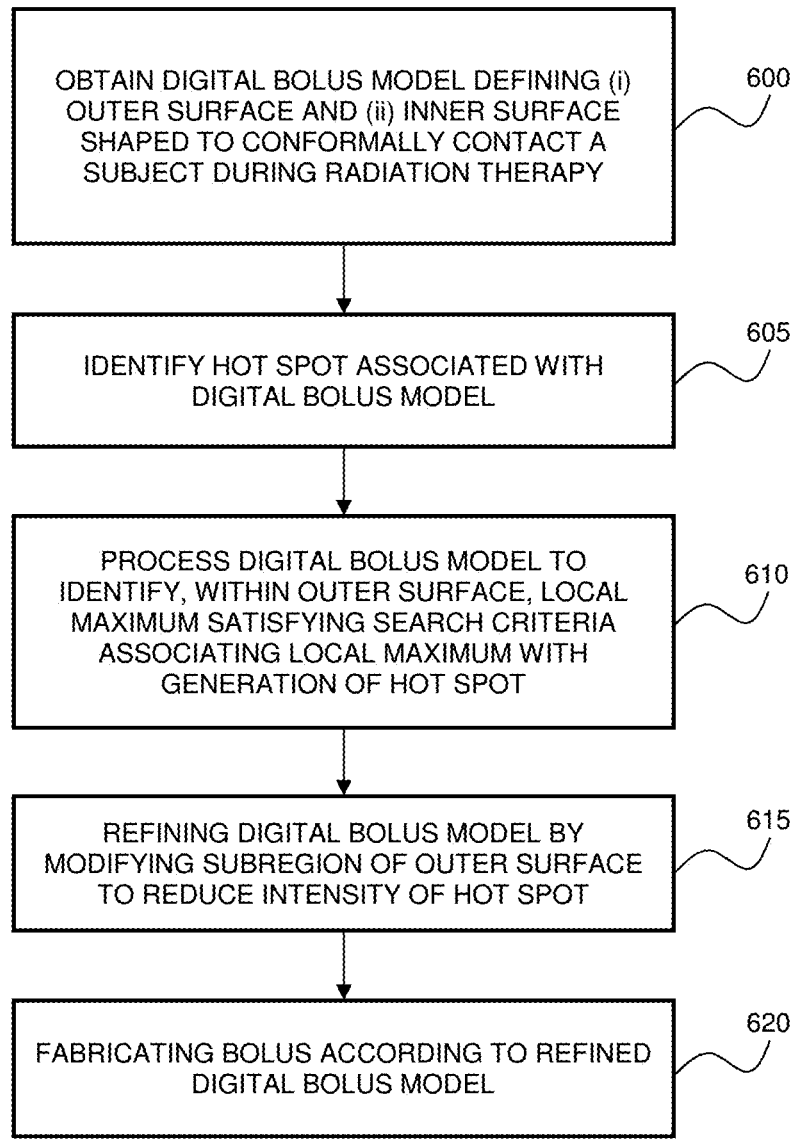
FIG. 10 is a flow chart illustrating an example method of refining a digital bolus model to reduce the intensity of a hot spot based on peak identification and smoothing.

A hot spot associated with the digital bolus model is identified, as shown at step 605 in FIG. 10. As noted above, the hot spot may be identified according to various different methods, such as, but not limited to (i) the processing of a dose distribution obtained from a treatment planning system, (ii) a hot spot RT structure obtained from a treatment planning system, and (iii) the calculation of a dose distribution based on the bolus model (such as via a pencil beam calculation).

The digital bolus model is processed to identify, within the outer surface, a local maximum satisfying search criteria, as shown at 610. The search criteria is provided such that when the search criteria is satisfied by a local maximum and a hot spot, it is likely that the hot spot is generated, at least in part, due to scattering from the local maximum. One example method of performing the identification of a local maximum (peak) is described above with reference to FIGS. 7A-7E. It will be understood that the example method disclosed in FIGS. 7A-7E merely provides one possible method of peak identification and bolus modification and that alternative methods of peak identification and bolus modification may be performed without departing from the intended scope of the present disclosure.

In some embodiments, the method outlined in FIG. 10 may be performed such that the search criteria involves a relative proximity of at least one local maximum measure associated with the local maximum and at least one hot spot measure associated with the hot spot. The local maximum location measure may be any positional or spatial measure associated with the local maximum, such as, but not limited to, the peak location, a contour surrounding the local maximum (e.g. a base contour associated with a valley adjacent to the local maximum), or a projection of these measures onto a reference plane. Similarly, the hot spot location measure may be any positional or spatial measure associated with the hot spot, such as, but not limited to, the hot spot center location and a margin surrounding the hot spot, or a projection of these measures onto a reference plane.

In the example method shown in FIGS. 7A-7E, the local maximum location measure is defined by the base contour and the hot spot location measure is provided by the hot spot search margin (when projected onto the reference plane), and the proximity criteria is satisfied when the local maximum location measure spatially overlaps with the hot spot location measure.

In one example implementation, the local maximum location measure may be the location of the local maximum on the outer surface of the digital bolus model, the hot spot location measure may be the location of the center of the hot spot (e.g. within the PTV), and the proximity criteria may be satisfied when the distance between the local maximum and the hot spot (determined without the use of a projection onto a common plane) lies below a threshold distance.

In another example implementation, the local maximum location measure may be location of the local maximum on the outer surface of the digital bolus model when projected onto a reference plane that is perpendicular to the beam axis, the hot spot location measure may be the location of the center of the hot spot (e.g. within the PTV) when projected onto the reference plane, and the proximity criteria may be satisfied when the distance between the projected local maximum and projected the hot spot (as determined within reference plane) lies below a threshold distance.

In another example implementation, the local maximum location measure may be the location of the local maximum on the outer surface of the digital bolus model when projected onto a reference plane that is perpendicular to the beam axis, the hot spot location measure may be the location of a search margin surrounding the hot spot, when the search margin is projected onto the reference plane, and the proximity criteria may be satisfied when the projection of the local maximum lies within the projection of the hot spot search margin (determined within reference plane) lies below a threshold distance.

In one example implementation, the local maximum location measure may be the location of the local maximum on the outer surface and the hot spot location measure may be provided by the intersection of a cone with the outer surface of the bolus, where the cone has a vertex located at the center of the hot spot and has an axis parallel to the beam axis. In such an example implementation, the proximity criteria may be satisfied when the local maximum lies with the curve defined by the projection of the cone with the outer surface of the bolus, and the cone angle may be user-configurable.

The preceding non-limiting examples demonstrate many different methods for determining when a local maximum and a hot spot satisfy search criteria. Referring again to FIG. 10, after having identified a local maximum associated with a hot spot, the digital bolus model may be modified by modifying (e.g. smoothing) the outer surface within a region that surrounds (and includes the local maximum), as shown at step 615. As described above, this modification may be performed according to many different example methods, including, but not limited to, scaling by a single factor or applying a scaling function that depends on a linear or non-linear distance from the location of the local maximum.

As shown in step 620 of FIG. 10, the refined digital bolus model, having undergone a local modification of its outer surface for hot spot intensity reduction, may be employed to fabricate a bolus for use in radiation therapy.

Although various example embodiments of the present disclosure describe the design and manufacture of an electron therapy radiation bolus, it will be understood that a radiation therapy bolus can be constructed for several different types of radiation therapy. For example, a bolus can be constructed for use in photon therapy or in particle-based radiation therapy such as, but not limited to, electron therapy and proton therapy. The propagation and other characteristics of photons, electrons, and protons are different. Thus, different bolus shapes, sizes, thicknesses, and/or constructions can be used to target a treatment dose of radiation to a same body region using different radiation therapies.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Improved Hot Spot Correction with Test Bolus and Planar Phantom

In the present example, 6 cases (5 phantom cases and 1 patient case) undergoing electron RT treatment planning were calculated with electron Monte Carlo algorithm (Eclipse, Varian Medical Systems, Palo Alto, Calif.) using simple bolus (5 mm), MEB (modulated electron bolus; i.e. an initial bolus design for achieving PTV conformity but possessing one or more hot spots), and hot-spot corrected MEB with different peak-to-valley ratios. In 5 phantom data sets, different shaped PTVs were delineated in order to produce different shapes of a modulated bolus. A 12 MeV electron beam, a volume-based optimization (D90% to V99.9%) and SSD=105 cm were used in all 6 cases. All plans were evaluated for maximum, minimum and mean dose to the PTV, conformity and homogeneity indices. Influence of the peak-to-valley ratio of the hot-spot corrected MEBs on dose conformity and homogeneity were evaluated.

In all 6 data sets, plans calculated using a simple bolus (5 mm) resulted in the conformity index (VD90/VPTV) ranging between 2.07 in "Phantom case 3" case to 4.05 in "Phantom case 2". At the same time, the homogeneity index ((Dmax−D90)/D90) was maintained close to 0.1 for all simple bolus cases.

When MEBs were employed, conformity index was significantly improved in all plans ranging from 1.53 in "Phantom case 3" to 2.81 in "Phantom case 2". However, homogeneity index was degraded in all MEB plans compared to simple bolus cases, ranging from 0.25 in the "patient case" to 0.46 in "Phantom case 1", thus yielding hot-spots to PTV ranging from 112.8% in the "patient case" to 131.3 in the "Phantom case 1".

In all 6 data sets, plans with hot-spot-corrected MEBs were calculated ranging from 0% (maximally reduced) to 80% (minimally reduced) peak-to-valley ratio concerning reduction of the bolus peaks. For every data set, one plan with hot-spot corrected MEB (usually 40% peak-to-valley ratio) was presented, yielding a conformity index comparable to the corresponding MEB plan and at the same time resulting in homogeneity index comparable to the corresponding simple bolus plan. In other words, clinically acceptable and favourable levels of both dose conformity and homogeneity were achieved in all MERT cases using the new hot-spot correction algorithm.

Figure 11A:
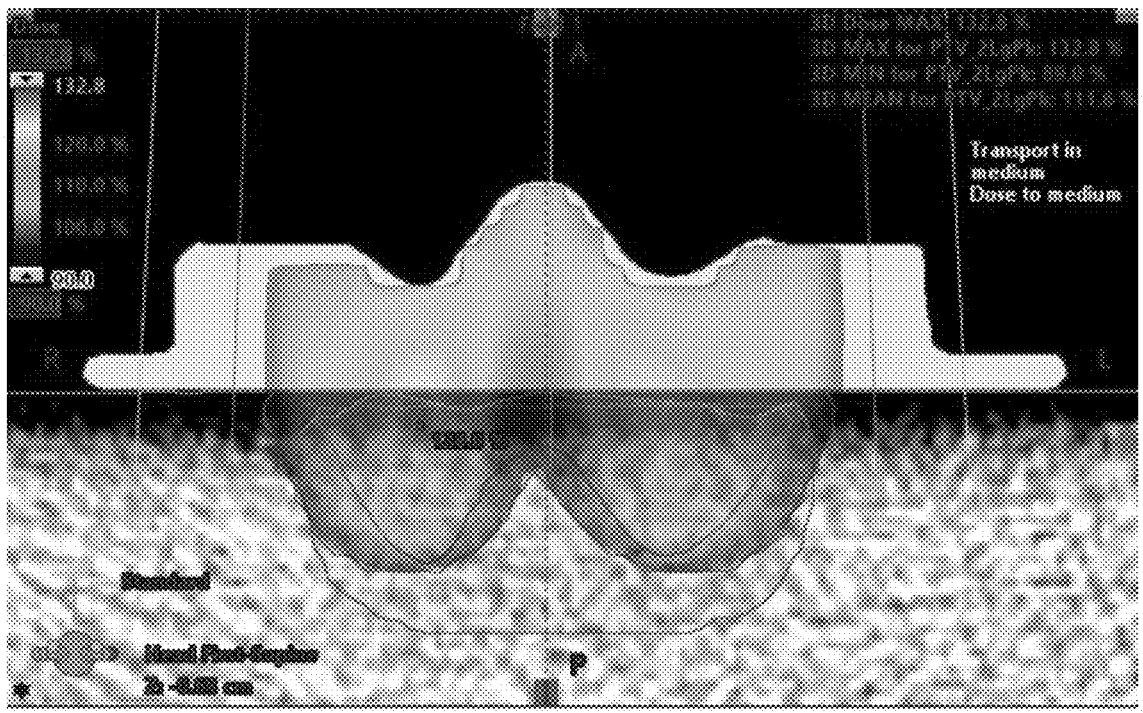
FIGS. 11A and 11B show dose and RT structure images associated with an electron radiation treatment plan involving an initial digital bolus model (FIG. 11A) and a refined digital bolus model (FIG. 11B) associated with a first phantom, in which an outer surface of the bolus was modified to reduce the intensity of a hot spot associated with a peak.
Figure 11B:
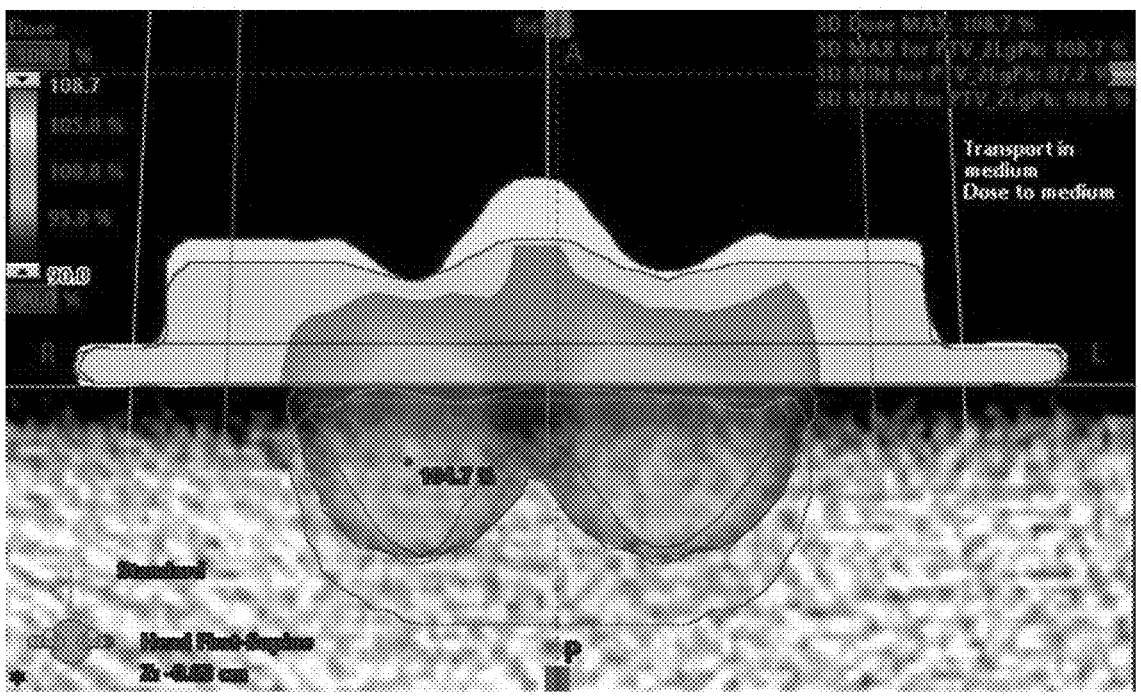
Figure 11C:
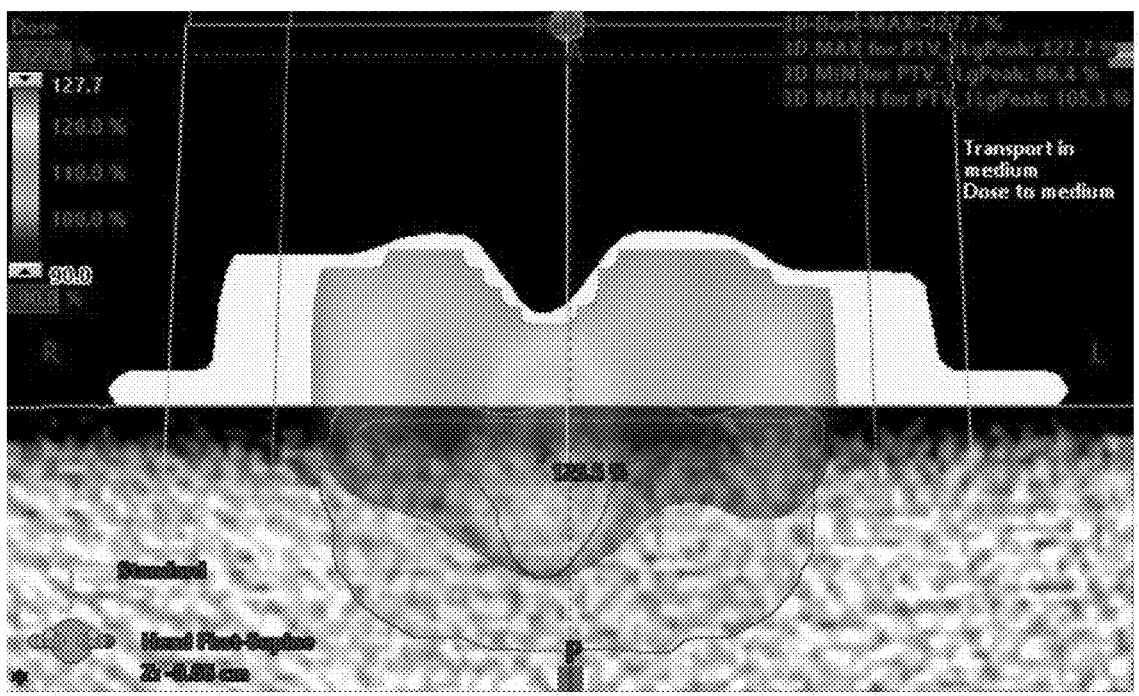
FIGS. 11C-11J show the initial and refined digital bolus models for the remaining 4 phantom cases.
Figure 11D:
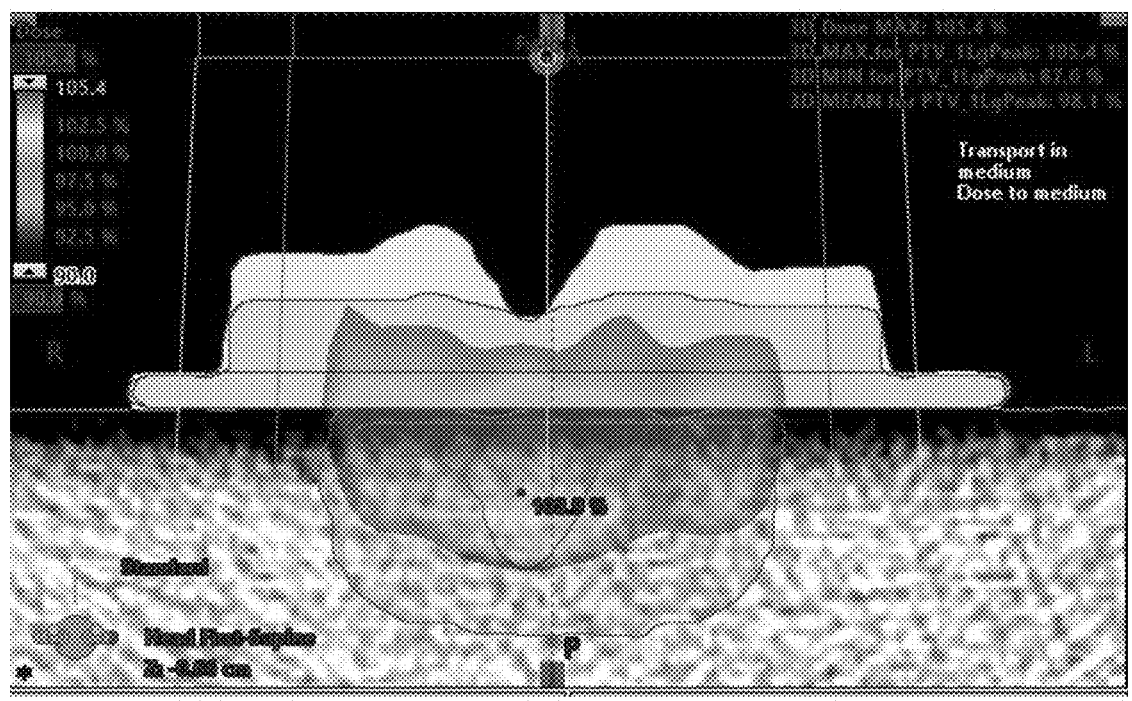
Figure 11E:
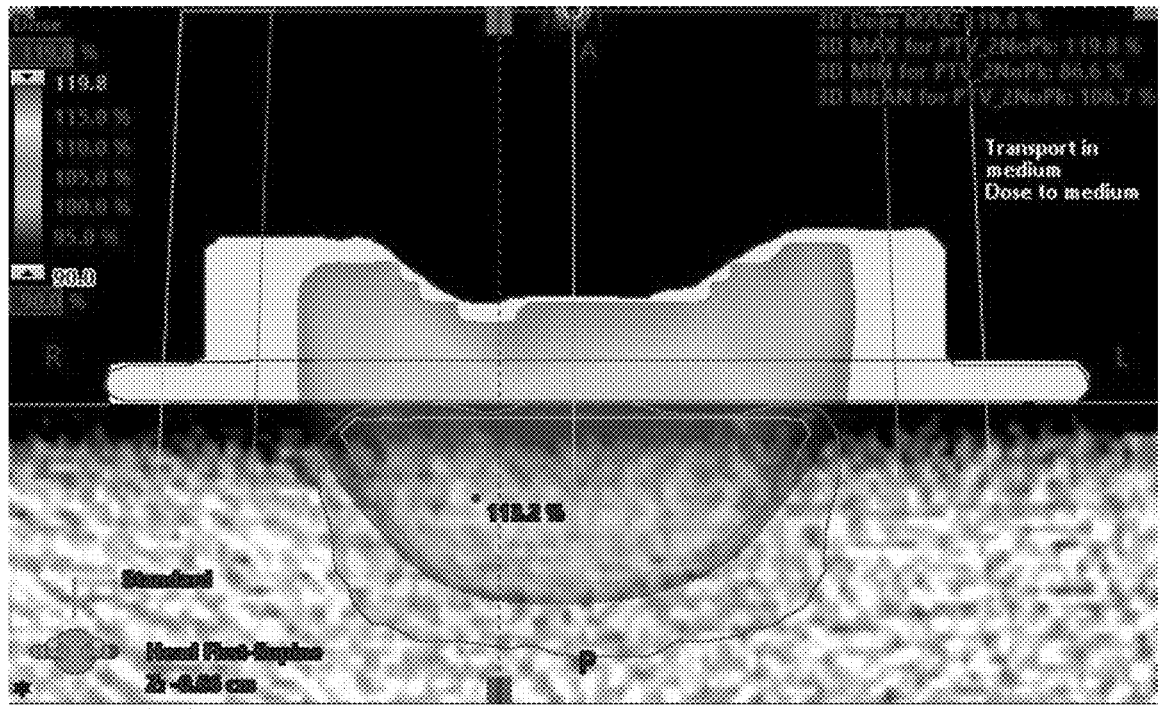
Figure 11F:
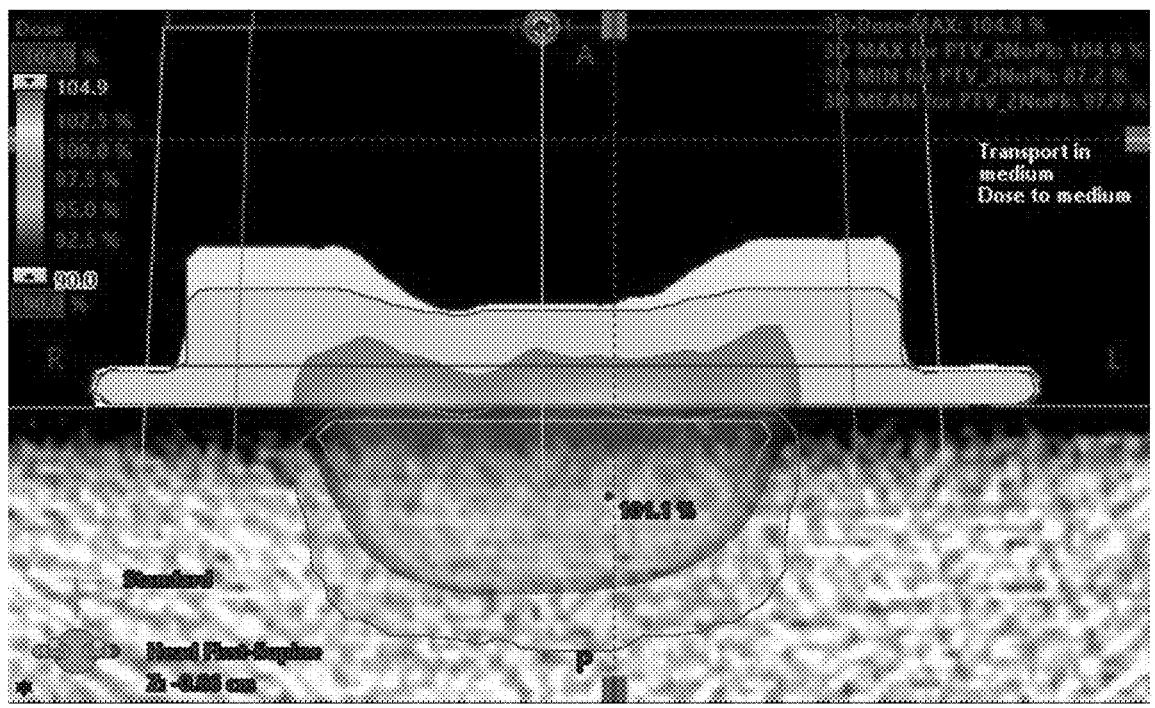
Figure 11G:
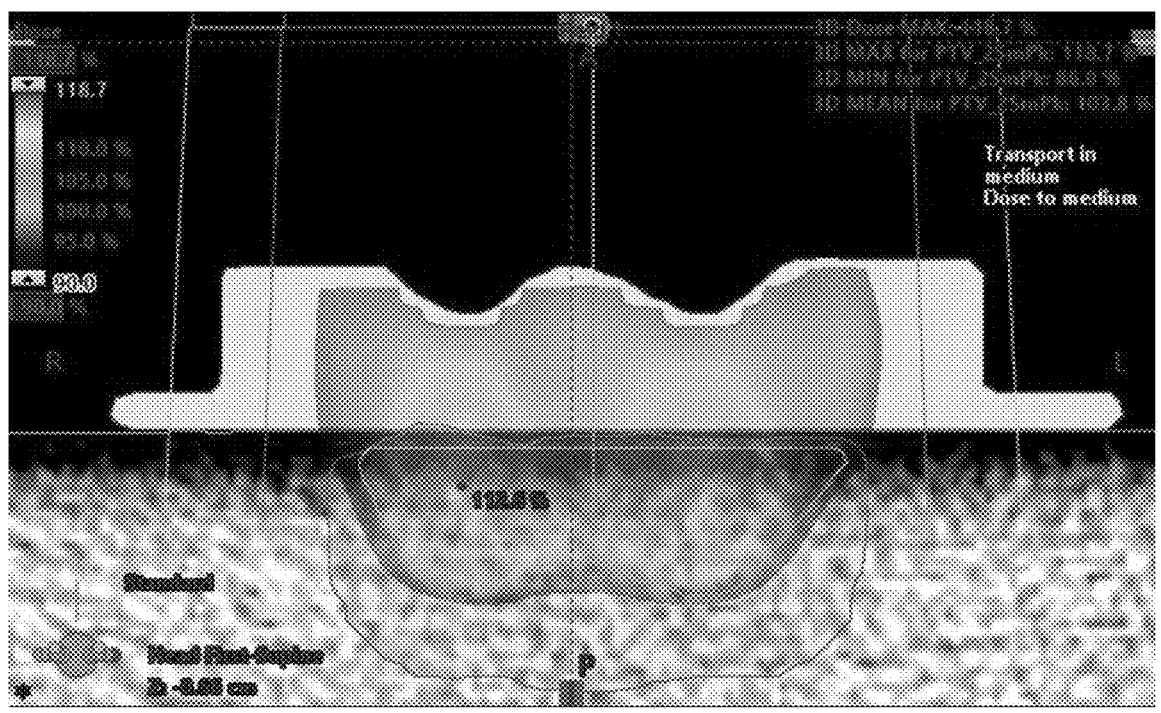
Figure 11H:
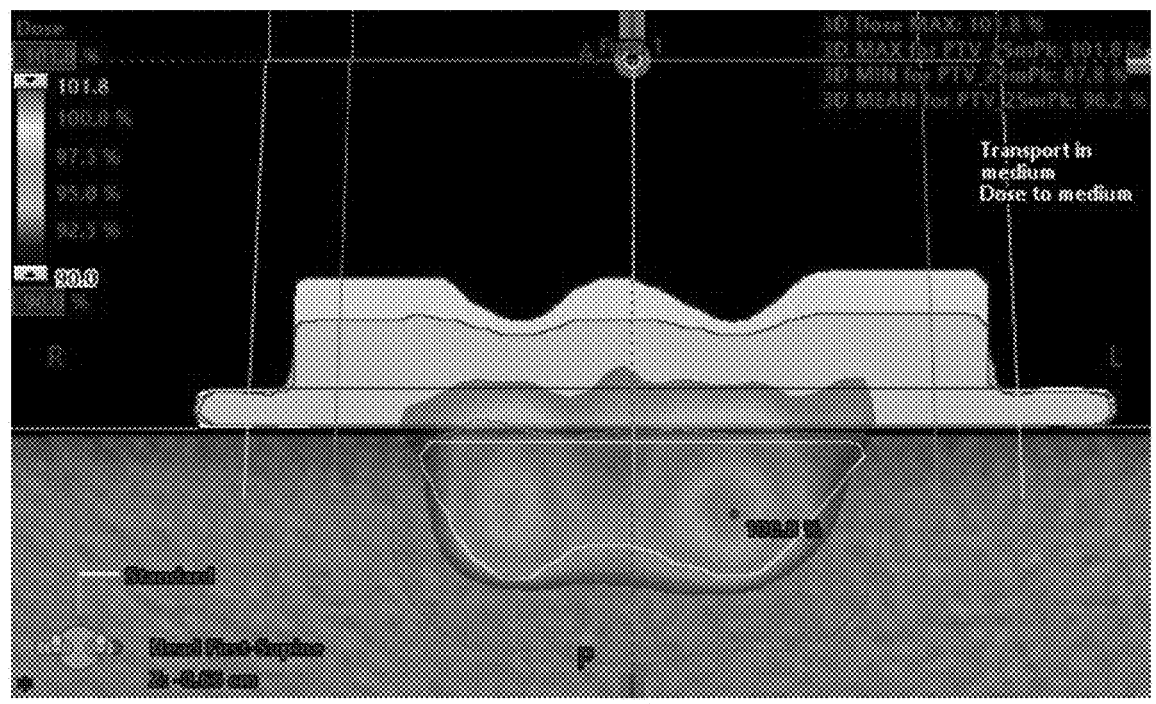
Figure 11I:
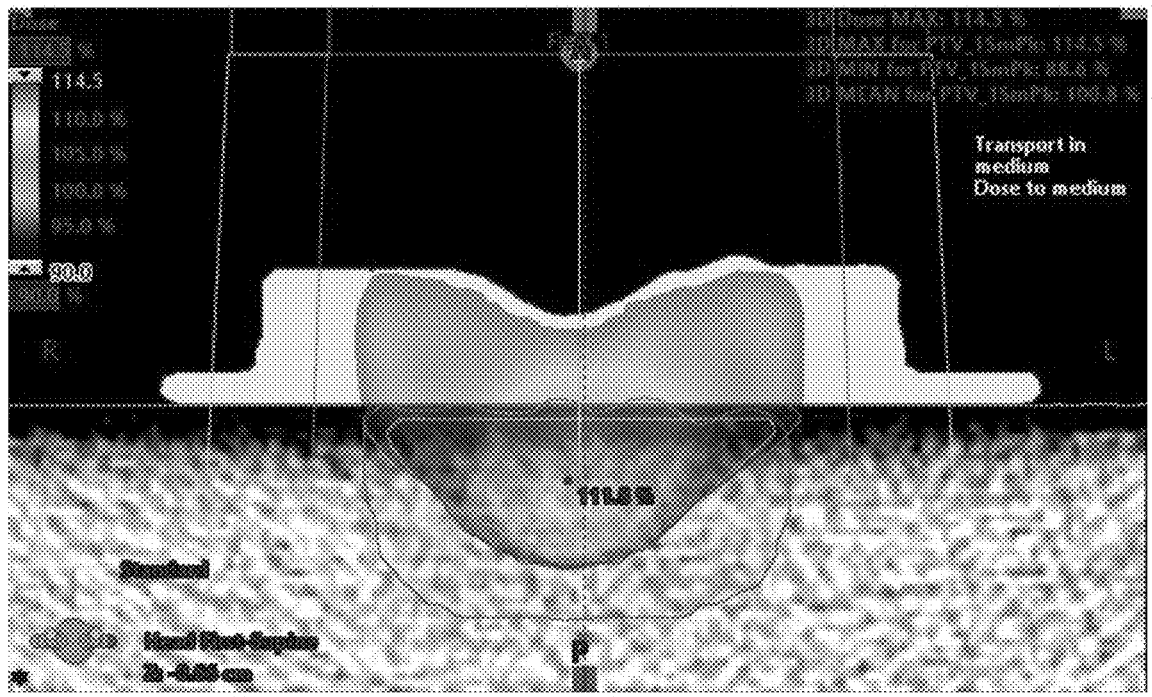
Figure 11J:
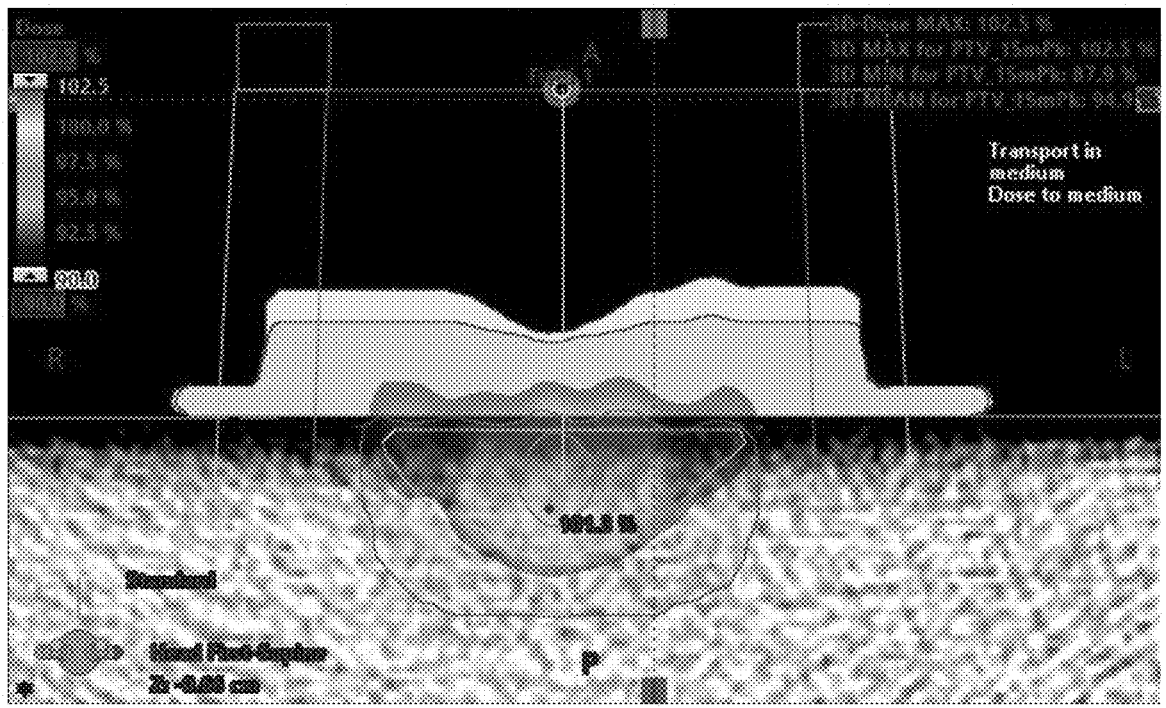

FIGS. 11A and 11B show results for the first phantom case, showing the 90% isodose contour (the mulicolour dose region) and also showing the 90% isodose contour for an initial simple bolus (the simple bolus structure is not shown). An initial digital bolus model was designed based on a refined simple digital bolus model, as shown in FIG. 11A, accounting for dose conformity to PTV but not addressing dose homogeneity. The digital bolus model, having a central peak and an adjacent valley, resulted in two hot spots, with one hot spot having an intensity of 130%. The hot spot reduction algorithm described above with reference to FIGS. 7A-7E was employed to identify the central peak as satisfying the proximity criteria associated with the hot spot in the reference plane. The peak was smoothed to generate a refined digital bolus model, as shown in FIG. 11B. After the modification of the digital bolus model to smooth the peak, the hot spot intensity was reduced to 105%. The outer surface of the bolus, in the region associated with the central peak, was smoothed to reduce the peak-to-valley ratio to 40% that ultimately reduced the amount of scattered electron radiation to the hot spot region. The shape of the prescribed dose conforming to PTV was maintained in the hot-spot corrected plan.

Figure 11K:
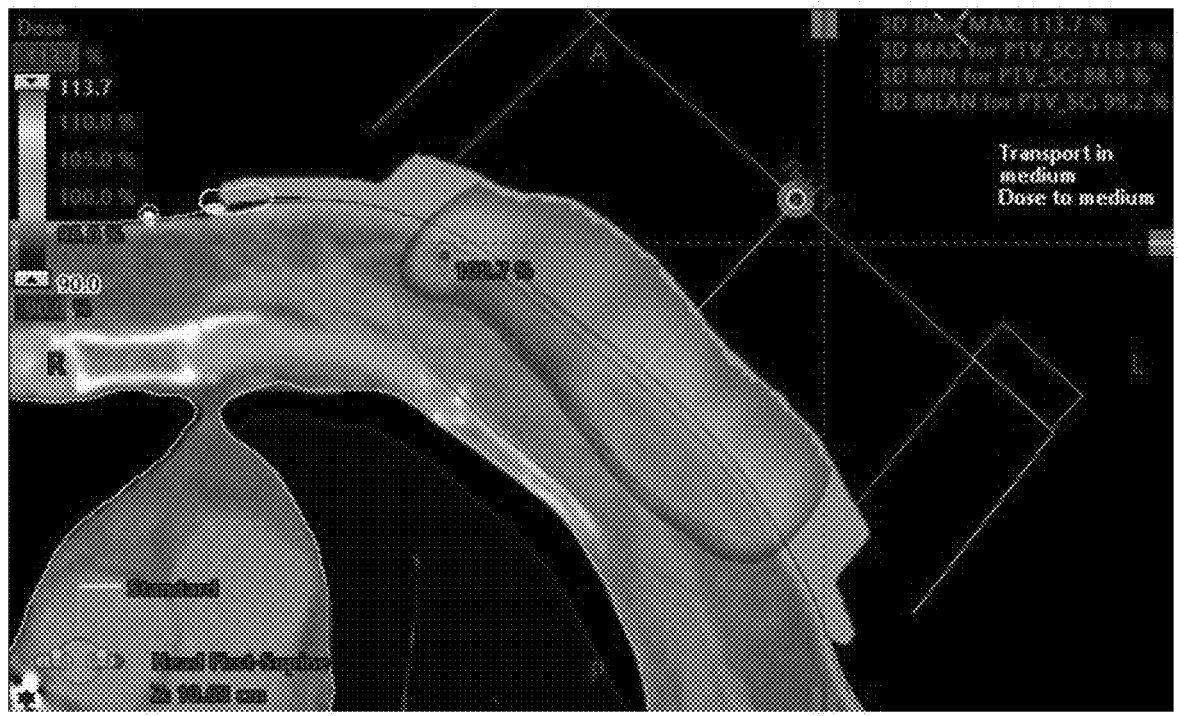
FIGS. 11K-11L the initial and refined digital bolus models for the example patient case.
Figure 11L:
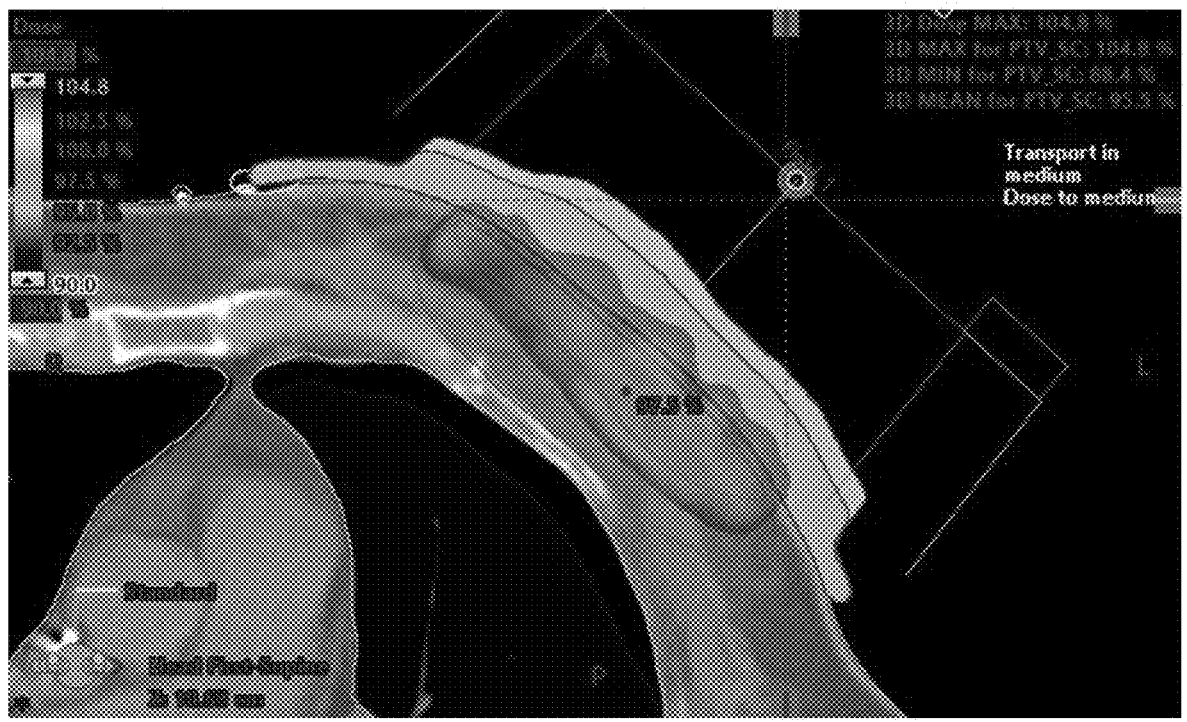

The initial and refined digital bolus models for the remaining 4 phantom cases are shown in FIGS. 11C and 11D, FIGS. 11E and 11F, FIGS. 11G and 11H, and FIGS. 11I and 11J, respectively. The initial and refined digital bolus models for the example patient case are shown in FIGS. 11K and 11L.

Figures 12, 13:
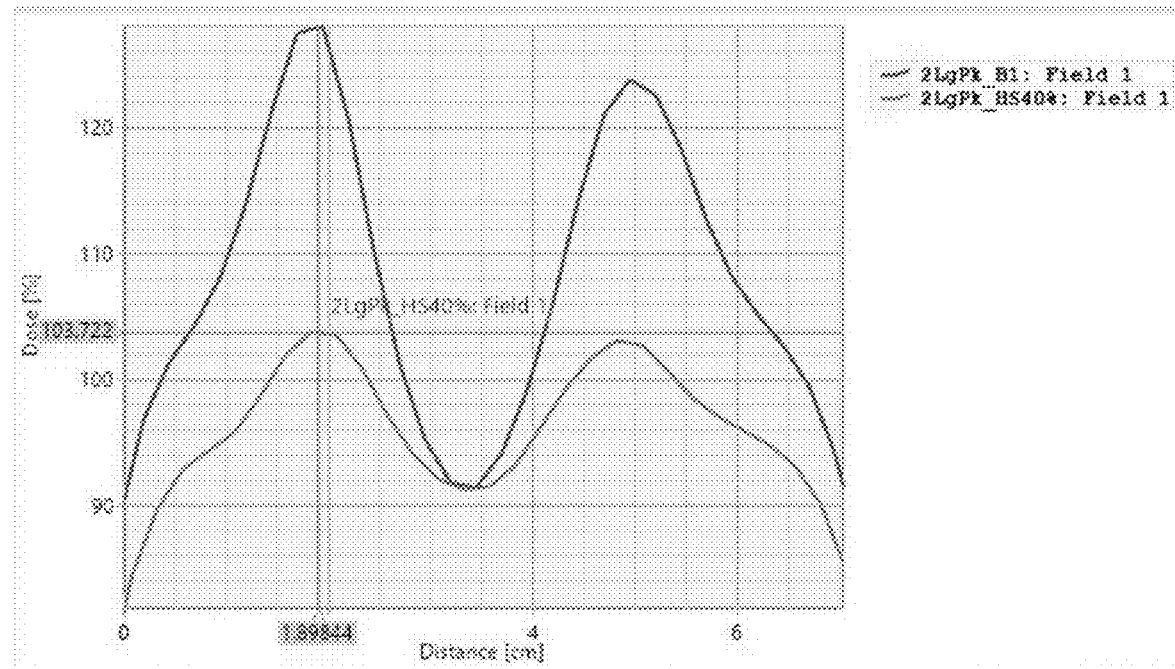
FIG. 12 plots a dosimetric comparison of the original MEB (modulated electron bolus) plan (red line) showing the severe hot spot region ~130% and the hot-spot corrected MEB (blue line) showing a reduced hot spot region (<105%) in the central axial plane.
FIG. 13 is a table presenting performance data of the present example hot spot reduction algorithm, showing how different peak reduction percentages (peak-to-valley ratios) of the hot spot corrected bolus influence clinical RT plan parameters.

FIG. 12 plots a dosimetric comparison of the original MEB (modulated electron bolus) plan (red line) showing the severe hot spot region ~130% and the hot-spot corrected MEB (blue line) for the first case (FIGS. 11A and 11B), showing a reduced hot spot region (<105%) in the central axial plane.

FIG. 13 is a table presenting performance data of the present example hot spot reduction algorithm for the first phantom case (FIGS. 11A and 11B), showing how different peak reduction percentages (peak-to-valley ratios) of the hot spot corrected bolus influence clinical RT plan parameters such as: maximum, minimum and mean dose in the plan, conformity and homogeneity indexes. All cases presented in the table employed 12 MeV electron beam, volume-based dose optimization of 90% of the prescribed dose to 99.9% of the PTV volume, SSD=105 cm, the same field size and block shape and the same distinct shape of the PTV as seen on FIGS. 11A-11B.

Overall, the present example demonstrates that by using different peak-reduction percentages within the present example algorithm, the maximum dose to PTV in the hot spot corrected MEB plan can be reduced while maintaining the level of dose conformity to PTV that is comparable to the original MEB plan. The example also demonstrates that a certain trade-off may exist between dose homogeneity and dose conformity to PTV in the hot-spot corrected plan. Therefore, in some example implementations, it may be beneficial to employ a plurality of different peak modifications (e.g. a set of different peak-reduction percentages; peak-to-valley ratios, or different scaling functions) to generate a set of output measures (e.g. those shown in FIG. 13, or variations thereof), from with a user select a preferred modified bolus design that achieves a desired balance between dose homogeneity and conformity to PTV depending on the clinical needs for a particular RT plan.

The present example methods of hot spot reduction via refinement of a digital bolus model may lead to improved quality of electron RT treatment plans that would otherwise be unfeasible or clinically unacceptable, ensuring patients receive the optimal cancer treatment modality. Moreover, the present example embodiments, and variations thereof, may be beneficial in substantially reducing the time of an existing manual designing of the hot-spot-corrected MEB from several hours to minutes (e.g. less than 10 minutes).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method of fabricating a bolus for use in radiation therapy, the method comprising:
   obtaining a digital bolus model, the digital bolus model defining an outer surface and an inner surface, wherein the inner surface is shaped to conformally contact a subject during radiation therapy;
   identifying a hotspot associated with the digital bolus model;
   processing the digital bolus model to identify, within the outer surface, a local maximum satisfying search criteria, the search criteria associating the local maximum with generation of the hotspot;
   refining the digital bolus model by modifying a subregion of the outer surface to reduce an intensity of the hotspot, the subregion including the local maximum, thereby obtaining a refined digital bolus model; and
   fabricating the bolus according to the refined digital bolus model.

2. The method according to claim 1 wherein the local maximum is determined to satisfy the search criteria associated with the hotspot by:
   determining a hotspot location measure associated with a location of the hotspot and a local maximum location measure associated with a location of the local maximum; and
   determining that the hotspot location measure and the local maximum location measure satisfy proximity criteria.

3. The method according to claim 2 wherein determining that the hotspot location measure and the local maximum location measure satisfy proximity criteria comprises:
   projecting one or both of the hotspot location measure and the local maximum location measure, such that after projection, the hotspot location measure and the local maximum location measure reside within a common two-dimensional region; and
   determining that the hotspot location measure and the local maximum location measure satisfy the proximity criteria within the common two-dimensional region.

4. The method according to claim 2 wherein the local maximum is determined to satisfy the proximity criteria associated with the hotspot by:
   projecting the hotspot location measure onto the outer surface, thereby obtaining a projected hotspot location measure; and
   determining that the projected hotspot location measure and the local maximum location measure satisfy the proximity criteria.

5. The method according to claim 2 wherein the local maximum is determined to satisfy the proximity criteria associated with the hotspot by:
   projecting the hotspot location measure and the local maximum location measure onto a reference plane that is perpendicular to a beam axis defined by a treatment plan associated with the subject, thereby obtaining a projected hotspot location measure and a projected local maximum location measure; and
   determining that the projected hotspot location measure and the projected local maximum location measure satisfy the proximity criteria.

6. The method according to claim 5 wherein the hotspot location measure is a location of a center of the hotspot and the local maximum location measure is a location of the local maximum, wherein determining that the projected hotspot location measure and the projected local maximum location measure satisfy proximity criteria comprises determining that a projection of the location of the center of the hotspot onto the reference plane and a projection of the location of the local maximum onto the reference plane have a separation less than a separation threshold.

7. The method according to claim 5 wherein the hotspot location measure is a three-dimensional hotspot margin surrounding the hotspot, and wherein determining that the projected hotspot location measure and the projected local maximum location measure satisfy proximity criteria comprises determining that a projection of the three-dimensional hotspot margin onto the reference plane spatially overlaps with a projection of the local maximum location measure onto the reference plane.

8. The method according to claim 7 wherein the three-dimensional hotspot margin is user-configurable.

9. The method according to claim 7 further comprising displaying, in a user interface, a visual representation of the three-dimensional hotspot margin.

10. The method according to claim 7 wherein the local maximum location measure demarcates a peak region surrounding the local maximum, and wherein determining that the projected hotspot location measure and the projected local maximum location measure satisfy proximity criteria comprises determining that the projection of the three-dimensional hotspot margin onto the reference plane spatially overlaps with a projection of the peak region surrounding the local maximum.

11. The method according to claim 10 wherein the peak region is user-configurable.

12. The method according to claim 10 wherein the peak region extends to a valley, such that beyond the valley, a height contour associated with the outer surface does not enclose the local maximum.

13. The method according to claim 12 wherein the subregion over which the outer surface is modified is the peak region.

14. The method according to claim 5 wherein the reference plane tangentially contacts the subject.

15. The method according to claim 1 wherein the local maximum is identified by:
obtaining height data characterizing a height of the outer surface relative to a height evaluation plane, wherein the height evaluation plane is perpendicular to the beam axis; and
processing the height data to locate the local maximum.

16. The method according to claim 15 wherein the outer surface is modified with the subregion by smoothing the outer surface within the subregion to reduce a height of the local maximum.

17. The method according to claim 15 wherein the height evaluation plane tangentially contacts the subject.

18. The method according to claim 1 wherein the hotspot is identified based on a hotspot RT structure exported by a treatment planning system.

19. The method according to claim 1 wherein the hotspot is identified by processing dose data obtained from a treatment planning system.

20. The method according to claim 1 wherein the hotspot is identified by processing dose data obtained by performing a pencil beam dose calculation.

21. The method according to claim 1 wherein the hotspot is identified, at least in part, based on input received from a user.

22. The method according to claim 1 further comprising receiving input from a user, the input confirming the association of the local maximum with the hotspot, prior to refining the digital bolus model.

23. The method according to claim 1 further comprising, prior to fabricating the bolus, exporting the refined digital bolus model to a treatment planning system to repeat a dose calculation based on the refined digital bolus model.

24. A system for modifying a digital bolus model for use in radiation therapy, the system comprising:
control and processing circuitry comprising at least one processors and associated memory, wherein said at least one processor is configured to execute instructions stored in the memory for performing the steps of:
identifying a hotspot associated with a digital bolus model, the digital bolus model defining an outer surface and an inner surface, wherein the inner surface is shaped to conformally contact a subject during radiation therapy;
processing the digital bolus model to identify, within the outer surface, a local maximum satisfying search criteria, the search criteria associating the local maximum with generation of the hotspot; and
refining the digital bolus model by modifying a subregion of the outer surface to reduce an intensity of the hotspot, the subregion including the local maximum, thereby obtaining a refined digital bolus model.

25. The system according to claim 24 wherein said control and processing circuitry is configured such that the local maximum is determined to satisfy the search criteria associated with the hotspot by:
determining a hotspot location measure associated with a location of the hotspot and a local maximum location measure associated with a location of the local maximum;
determining that the hotspot location measure and the local maximum location measure satisfy proximity criteria.

26. The system according to claim 25 wherein said control and processing circuitry is configured such that determining that the hotspot location measure and the local maximum location measure satisfy proximity criteria comprises:
projecting one or both of the hotspot location measure and the local maximum location measure, such that after projection, the hotspot location measure and the local maximum location measure reside within a common two-dimensional region; and
determining that the hotspot location measure and the local maximum location measure satisfy the proximity criteria within the common two-dimensional region.

27. The system according to claim 25 wherein said control and processing circuitry is configured such that the local maximum is determined to satisfy the proximity criteria associated with the hotspot by:
projecting the hotspot location measure onto the outer surface, thereby obtaining a projected hotspot location measure; and
determining that the projected hotspot location measure and the local maximum location measure satisfy the proximity criteria.

28. The system according to claim 25 wherein said control and processing circuitry is configured such that the local maximum is determined to satisfy the proximity criteria associated with the hotspot by:
projecting the hotspot location measure and the local maximum location measure onto a reference plane that is perpendicular to a beam axis defined by a treatment plan associated with the subject, thereby obtaining a projected hotspot location measure and a projected local maximum location measure; and
determining that the projected hotspot location measure and the projected local maximum location measure satisfy the proximity criteria.

29. The system according to claim 28 wherein said control and processing circuitry is configured such that the hotspot location measure is a location of a center of the hotspot and the local maximum location measure is a location of the local maximum, and such that determining that the projected hotspot location measure and the projected local maximum location measure satisfy proximity criteria comprises determining that a projection of the location of the center of the hotspot onto the reference plane and a projection of the location of the local maximum onto the reference plane have a separation less than a separation threshold.

30. The system according to claim 28 wherein said control and processing circuitry is configured such that the hotspot location measure is a three-dimensional hotspot margin surrounding the hotspot, and such that determining that the projected hotspot location measure and the projected local maximum location measure satisfy proximity criteria comprises determining that a projection of the three-dimensional hotspot margin onto the reference plane spatially overlaps with a projection of the local maximum location measure onto the reference plane.

31. The system according to claim 30 wherein said control and processing circuitry is configured such that the local maximum location measure demarcates a peak region surrounding the local maximum, and such that determining that the projected hotspot location measure and the projected local maximum location measure satisfy proximity criteria comprises determining that the projection of the three-dimensional hotspot margin onto the reference plane spatially overlaps with a projection of the peak region surrounding the local maximum.

32. The system according to claim 31 wherein said control and processing circuitry is configured such that the peak region extends to a valley, such that beyond the valley, a height contour associated with the outer surface does not enclose the local maximum.

33. The system according to claim 24 wherein said control and processing circuitry is operably connectable to a treatment planning system for obtaining the digital bolus model.

34. A method of refining a digital bolus model for use in radiation therapy, the method comprising:

obtaining a digital bolus model, the digital bolus model defining an outer surface and an inner surface, wherein the inner surface is shaped to conformally contact a subject during radiation therapy;

identifying a hotspot associated with the digital bolus model;

processing the digital bolus model to identify, within the outer surface, a local maximum satisfying search criteria, the search criteria associating the local maximum with generation of the hotspot; and refining the digital bolus model by modifying a subregion of the outer surface to reduce an intensity of the hotspot, the subregion including the local maximum, thereby obtaining a refined digital bolus model.

* * * * *